(12) United States Patent
Hatakeyama et al.

(10) Patent No.: US 8,576,081 B2
(45) Date of Patent: Nov. 5, 2013

(54) PHYSIOLOGICAL CONDITION ESTIMATION DEVICE AND VEHICLE CONTROL DEVICE

(75) Inventors: Yoshiyuki Hatakeyama, Fuji (JP); Yutaka Hirano, Susono (JP); Hiroki Okamura, Susono (JP)

(73) Assignee: Toyota Jidosha Kabushiki Kaisha, Toyota-Shi (JP)

( * ) Notice: Subject to any disclaimer, the term of this patent is extended or adjusted under 35 U.S.C. 154(b) by 265 days.

(21) Appl. No.: 13/201,189

(22) PCT Filed: Jan. 20, 2010

(86) PCT No.: PCT/JP2010/050625
§ 371 (c)(1),
(2), (4) Date: Aug. 11, 2011

(87) PCT Pub. No.: WO2010/092860
PCT Pub. Date: Aug. 19, 2010

(65) Prior Publication Data
US 2011/0313259 A1    Dec. 22, 2011

(30) Foreign Application Priority Data

Feb. 13, 2009 (JP) ................ 2009-031205
Feb. 13, 2009 (JP) ................ 2009-031207

(51) Int. Cl.
*G08B 23/00* (2006.01)

(52) U.S. Cl.
USPC ........ 340/575; 340/576; 340/573.1; 351/200; 180/271

(58) Field of Classification Search
USPC ............... 340/575, 576, 573.1; 600/300, 558; 180/271; 351/200
See application file for complete search history.

(56) References Cited

U.S. PATENT DOCUMENTS 6,304,187 B1    10/2001    Pirim
6,717,518 B1     4/2004    Pirim
(Continued)

FOREIGN PATENT DOCUMENTS

CN    1291320 A     4/2001
CN    101030316 A   9/2007
(Continued)

OTHER PUBLICATIONS

Translation of International Preliminary Report on Patentability of PCT/JP2010/050625.

(Continued)

*Primary Examiner* — Brian Zimmerman
*Assistant Examiner* — Laura Nguyen
(74) *Attorney, Agent, or Firm* — Kenyon & Kenyon LLP

(57) ABSTRACT

Provided are a physiological condition estimation device and a vehicle control device capable of preventing an error in the operation of an apparatus, such as a vehicle, and improving the safety of the operation of the apparatus. The physiological condition estimation device includes an eye-open time acquiring unit that acquires the eye-open time of the driver, a variation calculating unit that acquires a variation in the eye-open time acquired by the eye-open time acquiring unit, and a drowsiness predicting unit that determines the physiological condition of the driver on the basis of the variation in the eye-open time acquired by the variation calculating unit. In this way, since the physiological condition is determined on the basis of the variation in the eye-open time, it is possible to detect a slight reduction in the arousal level and estimate a significant reduction in the arousal level to a value that will cause an error in the driving of the vehicle in the future.

27 Claims, 32 Drawing Sheets

(56) References Cited

U.S. PATENT DOCUMENTS

| | | | |
|---|---|---|---|
| 2004/0170304 A1* | 9/2004 | Haven et al. | 382/115 |
| 2009/0237257 A1* | 9/2009 | Yamada et al. | 340/575 |
| 2011/0216181 A1* | 9/2011 | Yoda et al. | 348/78 |

FOREIGN PATENT DOCUMENTS

| | | |
|---|---|---|
| JP | 07-241283 A | 9/1995 |
| JP | 2000-315287 A | 11/2000 |
| JP | 2002-509321 A | 3/2002 |
| JP | 2003-061939 A | 3/2003 |
| JP | 2004-341954 A | 12/2004 |
| JP | 2005-318372 A | 11/2005 |
| JP | 2006-109980 A | 4/2006 |
| JP | 2008-003789 A | 1/2008 |
| JP | 2008-065776 A | 3/2008 |
| JP | 2008-099884 A | 5/2008 |
| JP | 2008-165348 A | 7/2008 |

OTHER PUBLICATIONS

International Search Report mailed May 11, 2010 of PCT/JP2010/050625.

* cited by examiner

*Fig.4*

| START TIME | END TIME | EYE-OPEN TIME |
|---|---|---|
| $ts_1$ | $te_1$ | $to_1$ |
| $ts_2$ | $te_2$ | $to_2$ |
| $ts_3$ | $te_3$ | $to_3$ |
| ⋮ | ⋮ | ⋮ |
| $ts_{n-2}$ | $te_{n-2}$ | $to_{n-2}$ |
| $ts_{n-1}$ | $te_{n-1}$ | $to_{n-1}$ |
| $ts_n$ | $te_n$ | $to_n$ |

Fig.5
(a)
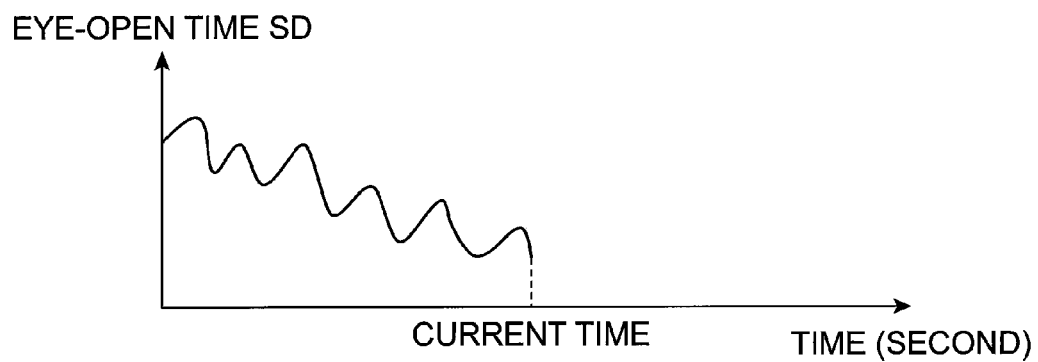
(b)
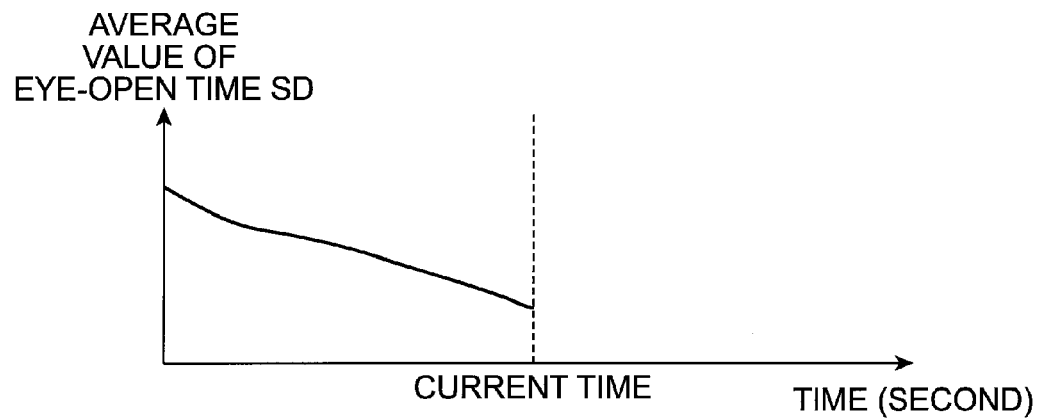

*Fig.6*
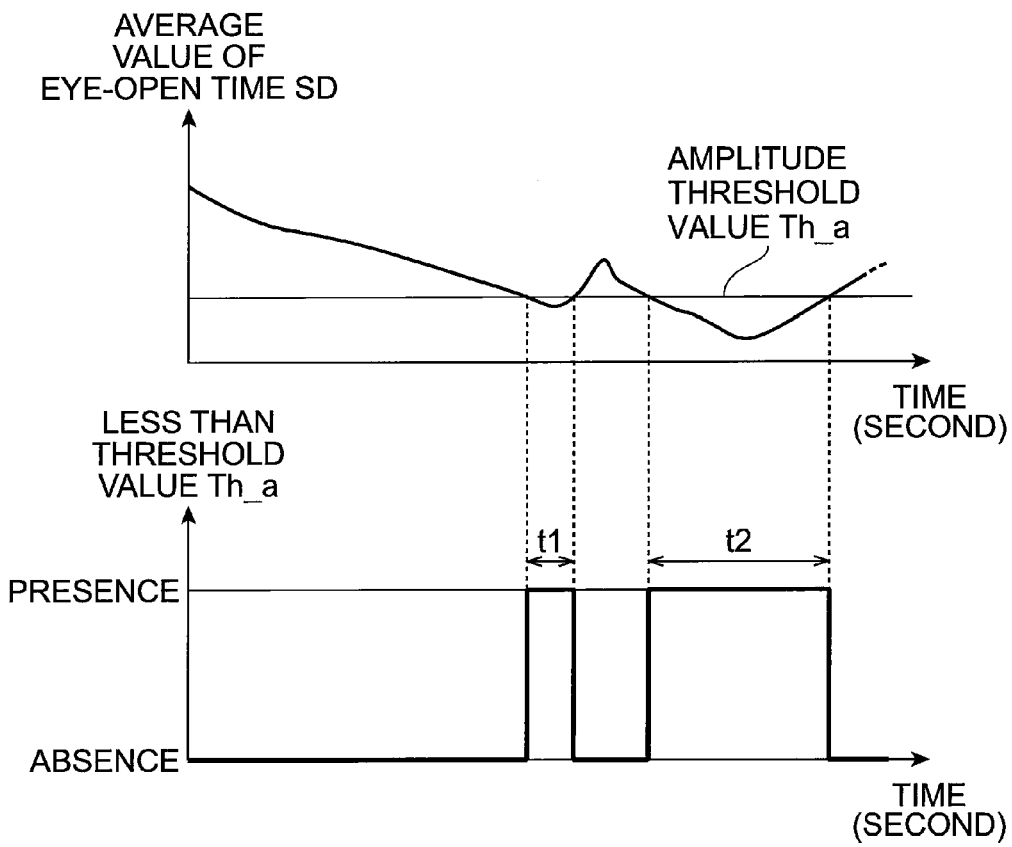
(a)
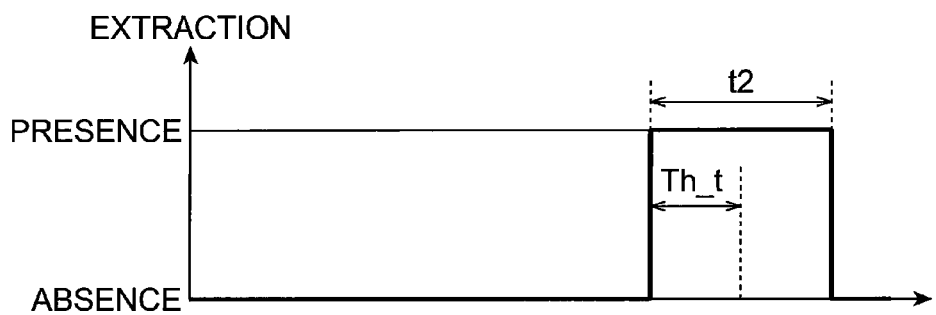
(b)

Fig.7
(a)
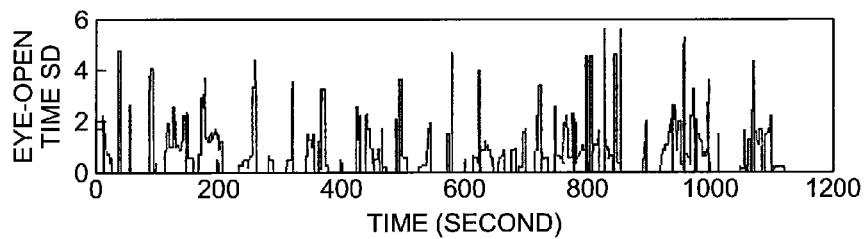
(b)
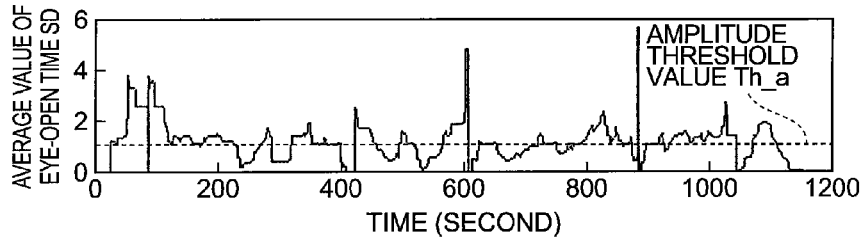
(c)
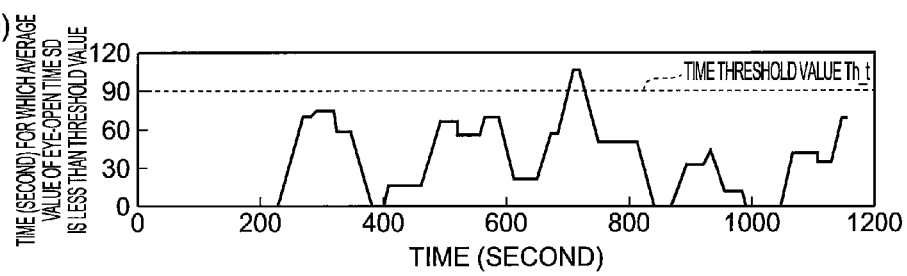
(d)
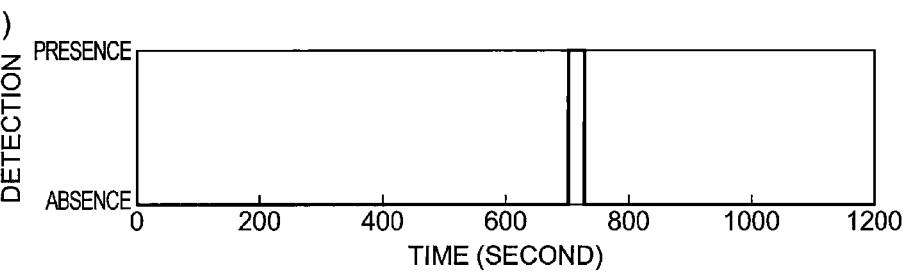
(e)
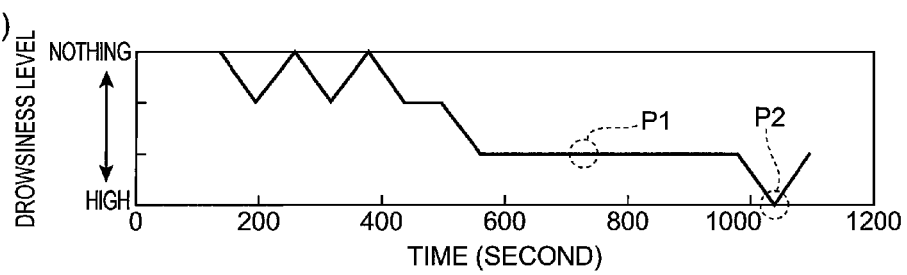

*Fig.10*

| EYE-OPENING NUMBER | EYE-OPEN TIME (SECOND) |
|---|---|
| 1 | 6.5 |
| 2 | 8.9 |
| 3 | 12 |
| 4 | 5.8 |
| 5 | 9.7 |
| 6 | 16 |

Fig.27
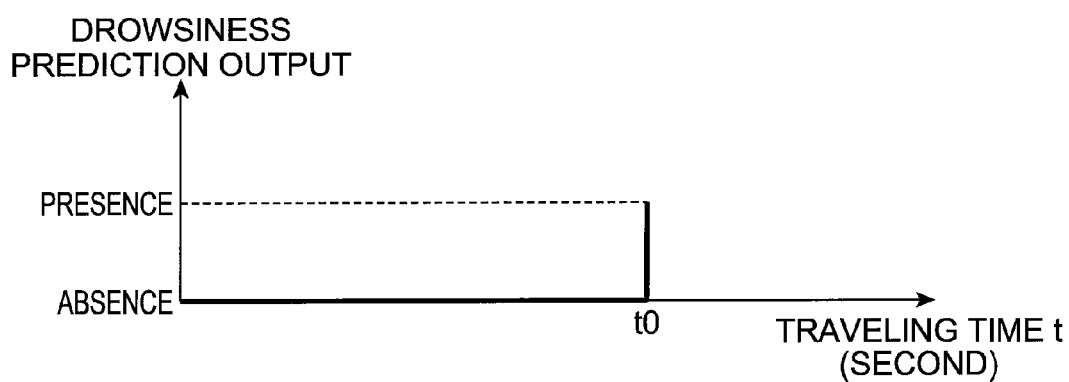
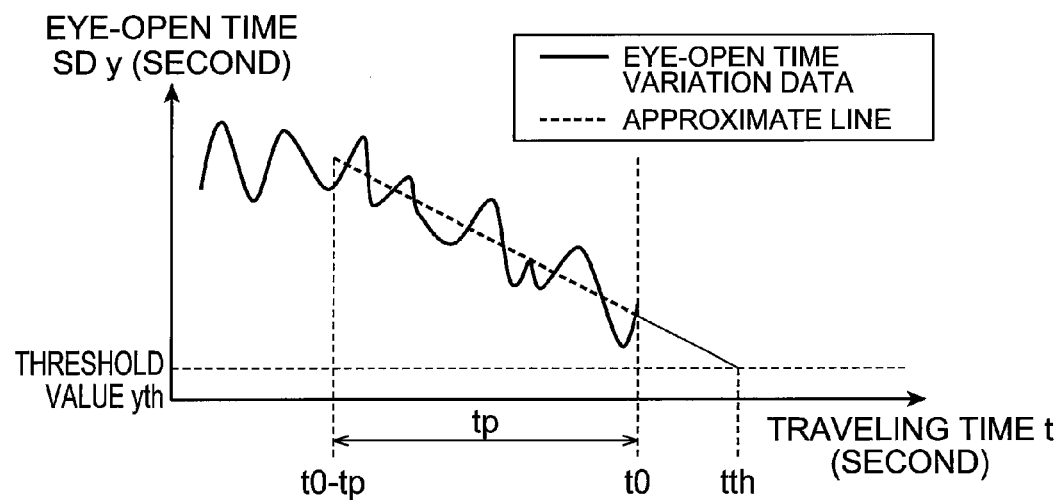

Fig.29

| PROCESS NAME | CONSTANT | NUMERICAL VALUE | UNIT |
|---|---|---|---|
| MODEL APPLICATION SECTION | tp | 500 | SECOND |
| GRADIENT DETERMINING SECTION | Gt | 0 | NOTHING |
| SLEEPING OCCURRENCE TIME CALCULATING SECTION | yth | 10 | SECOND |

PHYSIOLOGICAL CONDITION ESTIMATION DEVICE AND VEHICLE CONTROL DEVICE

This is a 371 national phase application of PCT/JP2010/050625 filed 20 Jan. 2010, which claims priority to Japanese Patent Applications No. 2009-031207 and 2009-031205, both filed on 13 Feb. 2009, the contents of which are incorporated herein by reference.

TECHNICAL FIELD

The present invention relates to a physiological condition estimation device that estimates the physiological condition of a target person and a vehicle control device that controls a vehicle on the basis of the physiological condition.

BACKGROUND ART

Patent Literature 1 discloses a physiological condition estimation device that estimates the physiological condition of a target person, such as the driver of a vehicle. The physiological condition estimation device calculates an eye-blink rate and the interval between eye blinks to calculate a log-transformed value, calculates the frequency distribution of the interval between eye blinks at a predetermined time interval, and calculates the standard deviation of the log-transformed value and the average value of the frequency distribution. In addition, the physiological condition estimation device determines an arousal-level reduced condition from a value obtained by dividing the standard deviation by the average value and the cluster eye blink determined from the time interval between eye blinks. The physiological condition estimation device determines the arousal-level reduced condition. The arousal-level reduced condition means a condition in which, as the eye-blink rate and the cluster eye-blink rate increase, the entire eye blink distribution becomes irregular. In addition, a physiological condition estimation device has been proposed which estimates attentiveness to video content and estimates the physiological condition of the driver (for example, see Patent Literature 2). Furthermore, a physiological condition estimation device has been proposed which estimates the arousal level from the ratio of the eye-closed time and the degree of the opening of the eye of the driver (for example, see Patent Literature 3).

CITATION LIST

Patent Literature

[Patent Literature 1] Japanese Unexamined Patent Application Publication No. 7-241283
[Patent Literature 2] Japanese Unexamined Patent Application Publication No. 2005-318372
[Patent Literature 3] Japanese Unexamined Patent Application Publication No. 2006-109980

SUMMARY OF INVENTION

Technical Problem

The estimation device using an increase in the eye-blink rate and the cluster eye-blink rate and irregularity in the eye blink distribution can detect a large reduction in the arousal level to a value that affects the operation of the vehicle. The estimation device using the ratio of the eye-closed time and the degree of the opening of the eye can also detect a large reduction in the arousal level. However, it is difficult for the physiological condition estimation device according to the related art to detect a slight reduction in the arousal level, which is the stage before the reduction in the arousal level affects the operation of the vehicle. Therefore, it is difficult for the physiological condition estimation device according to the related art to predict a large reduction in the arousal level in the future and alert the attention of the driver in advance. Therefore, it is difficult to prevent an error in the driving of the vehicle. As described above, the physiological condition estimation device according to the related art can detect a variation in the physiological condition that is sufficiently strong to affect the operation of the vehicle, but is incapable of detecting a slight variation in the physiological condition, which is the stage before the variation in the physiological condition affects the operation of the vehicle. Therefore, the physiological condition estimation device according to the related art has a problem in that it is difficult to prevent an error in the operation before the current operation is affected.

The invention has been made in order to solve the above-mentioned problems, and an object of the invention is to provide a physiological condition estimation device and a vehicle control device capable of preventing an error in the operation of an apparatus, such as a vehicle, and improving the safety of the operation of the apparatus.

Solution to Problem

The inventors conducted a study on a technique for solving the above-mentioned problems and found that the driver of the vehicle actively moved the eyes to check various surrounding conditions, such as signals, pedestrians, or other vehicles with a high arousal level or high attentiveness, for example, during the driving of the vehicle, and there was an increase in variation in the eye-open time (the time for which the eyes are open between eye blinks). In addition, the inventors found that, when the driver felt a little drowsy or the attentiveness of the driver was slightly reduced within the range in which driving was not affected, the eyes of the driver moved slowly to check the surrounding conditions and a variation in the eye-open time decreased. As a result, the inventors found that, when the physiological condition was estimated on the basis of the variation in the eye-open time, it was possible to detect a slight change that would cause a large variation in the physiological condition in the future which could not be detected in the related art.

According to an aspect of the invention, a physiological condition estimation device includes: an eye-open time acquiring unit that acquires an eye-open time of a target person; a variation acquiring unit that acquires a variation in the eye-open time acquired by the eye-open time acquiring unit; and a physiological condition determining unit that determines a physiological condition of the target person on the basis of the variation in the eye-open time acquired by the variation acquiring unit.

According to another aspect of the invention, there is provided a vehicle control device that controls a vehicle on the basis of a variation in the eye-open time of a target person.

According to the physiological condition estimation device, the eye-open time of the driver is acquired and the physiological condition is determined on the basis of a variation in the eye-open time. Therefore, it is possible to detect a slight change in the physiological condition and estimate preliminarily a significant reduction in the physiological condition to a value that may cause an error in the operation of an apparatus, such as a vehicle, in the future. In addition, the vehicle control device according to the invention controls the vehicle on the basis of a variation in the eye-open time of the driver. Therefore, it is possible to perform a drive assist process before an error occurs in the driving of the vehicle. In this way, it is possible to prevent an error in the operation of an apparatus, such as a vehicle, and thus improve the safety of the operation of the apparatus.

Specifically, in the physiological condition estimation device according to the above-mentioned aspect of the invention, the physiological condition determining unit may determine a condition in which the arousal level of the target person is higher as the magnitude of the variation in the eye-open time is larger and a condition in which the arousal level of the target person is lower as the magnitude of the variation in the eye-open time is smaller.

In the physiological condition estimation device according to the above-mentioned aspect of the invention, specifically, the physiological condition determining unit may determine drowsiness, a reduction in attentiveness, or a waking condition. When these physiological conditions are determined, it is possible to perform a drive assist process for ensuring safe driving.

In the physiological condition estimation device according to the above-mentioned aspect of the invention, the variation acquiring unit may perform a statistical process on the eye-open time from a standard deviation or a variance to calculate the variation in the eye-open time. As such, when the statistical process that changes the variation in the eye-open time into data is performed, it is possible to accurately or easily estimate the physiological condition.

In the physiological condition estimation device according to the above-mentioned aspect of the invention, the physiological condition determining unit may calculate an average value of the variation in the eye-open time to smooth data and may compare the calculated value with a predetermined threshold value to determine the physiological condition. According to this structure, it is possible to process the acquired information into data indicating the gradient of the variation in the eye-open time.

In the physiological condition estimation device according to the above-mentioned aspect of the invention, after physiological condition determining unit determines the condition in which the arousal level is low, the physiological condition estimation device may change an operation mode to a sleeping detection mode in which the drowsiness of the target person is directly detected. As described above, after predicting the occurrence of drowsiness in the future, the physiological condition estimation device changes the operation mode to the mode in which the drowsiness of the target person at the current time is monitored in real time. In this way, it is possible to accurately monitor the condition of the driver from a waking condition to the loss of consciousness and thus perform a proper drive assist process.

The physiological condition estimation device according to the above-mentioned aspect may further include a time width setting unit that sets a time width which is used by the variation acquiring unit to perform the statistical process, on the basis of data of a plurality of the eye-open times acquired by the eye-open time acquiring unit. According to this structure, it is possible to calculate the variation with a time width suitable for each object person. For example, when the time width for calculating the variation is set to a constant value, there is difficulty in having correspondence to the difference between the eye-open times of the individual object persons, and the accuracy of estimating the physiological condition of a specific object person is likely to be reduced. However, according to the physiological condition estimation device having the above-mentioned structure, it is possible to accurately estimate the physiological condition of everybody regardless of the difference between the individual object persons.

The physiological condition estimation device according to the above-mentioned aspect may further include: a maximum value deriving unit that derives a maximum value of the variation in the eye-open time and updates the maximum value; and a threshold value setting unit that sets the predetermined threshold value used by the physiological condition determining unit to determine the physiological condition, on the basis of the updated maximum value. For example, in the case of a target person with a long eye-open time, the variation in the eye-open time tends to increase. Therefore, when the predetermined threshold value is set to a constant value according to the target person with a short eye-open time, the variation in the eye-open time of the target person with a long eye-open time does not reach the predetermined threshold value. In this case, a reduction in the arousal level is less likely to be determined. On the other hand, when the predetermined threshold value is set according to the target person with a long eye-open time, there is a possibility that the arousal level of the target person with a short eye-open time is unnecessarily determined to be reduced. Therefore, when the predetermined threshold value is set to a constant value, there is difficulty in having correspondence to the difference between the variations in the eye-open time of the individual persons and estimate the physiological condition of everybody with high accuracy. However, in the physiological condition estimation device according to the invention, the predetermined threshold value is set on the basis of the maximum value of the variation in the eye-open time. Therefore, it is possible to have correspondence to the difference between the variations in the eye-open time of the individual persons and estimate the physiological condition of everybody with high accuracy. In addition, the maximum value for setting the predetermined threshold value is updated over time and the updated maximum value is set. For example, even when the driver is drowsy during the start of driving and the arousal level of the driver increases during driving, it is possible to accurately estimate the physiological condition of the driver according to the unique variation characteristics of the target person.

In the physiological condition estimation device according to the above-mentioned aspect of the invention, the physiological condition determining unit may determine that the attentiveness of the target person is reduced on the basis of an increase in the variation in the eye-open time. The attentiveness of the driver is reduced before the arousal level thereof is reduced. The variation in the eye-open time in an attentiveness-reduced condition is more than the variation in the eye-open time in a normal condition in which the attentiveness is not reduced. Therefore, the physiological condition determining unit can determine that the attentiveness of the target person is reduced on the basis of an increase in the variation in the eye-open time. In this way, the physiological condition estimation device according to the invention can estimate the physiological condition early before the arousal level of the target person is affected.

The physiological condition estimation device according to the above-mentioned aspect may further include a drowsiness occurrence possibility determining unit that determines whether there is a possibility of the target person reaching a drowsy condition after the physiological condition determining unit determines that the attentiveness is reduced. For example, even when determination is performed on the basis of an increase in the variation in the eye-open time, in some cases, the target person may not reach the drowsy condition in the future. For example, when it is determined that attentiveness is reduced and the drive assist process is performed without any exception, the target person is likely to become confused. Therefore, the drowsiness occurrence possibility determining unit determines whether there is a possibility of the target person reaching a drowsy condition. In this way, it is possible to prevent the drive assist process from being unnecessarily performed.

The physiological condition estimation device according to the above-mentioned aspect may further include a drowsiness occurrence estimating unit that estimates the time until the target person will reach a drowsy condition, on the basis of the amount of change of the variation in the eye-open time with respect to time, after the physiological condition determining unit determines that the attentiveness is reduced. The drowsiness occurrence estimating unit can estimate the time until the target person will reach a drowsy condition on the basis of the amount of change of the variation in the eye-open time with respect to time. In this way, the physiological condition estimation device according to the invention can perform an appropriate drive assist process on the basis of, for example, the estimated time.

According to another aspect of the invention, a physiological condition estimation device includes: an eye-open time acquiring unit that acquires an eye-open time of a target person; a variation acquiring unit that acquires a variation in the eye-open time acquired by the eye-open time acquiring unit; and a physiological condition estimating unit that estimates a physiological condition of the target person on the basis of the amount of change of the variation in the eye-open time acquired by the variation acquiring unit with respect to time.

According to another aspect of the invention, there is provided a vehicle control device that controls a vehicle on the basis of the amount of change of a variation in the eye-open time of a target person with respect to time.

The physiological condition estimation device according to the above-mentioned aspect acquires the eye-open time of the target person and estimates the physiological condition of the target person on the basis of the amount of change of the variation in the eye-open time with respect to time (for example, the gradient of a graph when the variation in the eye-open time is modeled as an approximate line). Therefore, it is possible to estimate that the arousal level will be significantly reduced to a value that may cause an error in the driving of the vehicle in the future even in the stage in which the arousal level is slightly reduced. In addition, the vehicle control device according to the invention can control a vehicle on the basis of the amount of change of the variation in the eye-open time of the driver with respect to time to perform a drive assist process before an error occurs in the driving of the vehicle. In this way, it is possible to improve the safety of the operation of an apparatus, such as a vehicle. When the physiological condition estimating unit estimates the physiological condition, the term "estimate" means acquiring a future physiological condition and is different from the term "determine the physiological condition" that means acquiring the current physiological condition.

In the physiological condition estimation device according to the above-mentioned aspect, the physiological condition estimating unit may estimate the time required for a change in the physiological condition on the basis of the amount of change of the variation in the eye-open time with respect to time. In this way, it is possible to estimate the time until the physiological condition will change to have an adverse effect on driving. Therefore, it is possible to perform an appropriate drive assist process on the basis of, for example, the time.

The physiological condition estimation device according to the above-mentioned aspect may further include an estimation result update unit that updates the time required for a change in the physiological condition on the basis of an increase or decrease in the amount of change of the variation in the eye-open time with respect to time. According to this structure, for example, the amount of change of the variation in the eye-open time with respect to time increases when the variation in the eye-open time is increasing. Therefore, in this case, it is possible to extend the estimated time until the physiological condition will change which is displayed to the target person or cancel the estimated time. On the other hand, the amount of change of the variation in the eye-open time with respect to time decreases when the variation in the eye-open time is decreasing. Therefore, in this case, it is possible to derive a new estimated time and update the estimated time. In this way, it is possible to reflect the latest eye-opening condition of the target person in the estimation result and thus improve the accuracy of estimation.

According to another aspect of the invention, a physiological condition estimation device includes: an eye-open time acquiring unit that acquires an eye-open time of a target person; a variation acquiring unit that acquires a variation in the eye-open time acquired by the eye-open time acquiring unit; and a physiological condition determining unit that determines a change in a physiological condition of the target person on the basis of the amount of change of the variation in the eye-open time acquired by the variation acquiring unit with respect to time.

The physiological condition estimation device according to the above-mentioned aspect can determine whether the physiological condition of the target person will change on the basis of the amount of change of the variation in the eye-open time with respect to time. For example, when the amount of change of the variation in the eye-open time with respect to time is reduced in the negative direction, it is determined that the arousal level of the target person is rapidly reduced and sleeping occurs or the target person is in an absentminded condition. It is possible to perform an appropriate drive assist process at the time when the determination is performed. On the other hand, when the amount of change of the variation in the eye-open time with respect to time increases in the positive direction, it is determined that the driver is in a waking condition and the drive assist process that is being currently performed may be cancelled, or the position of a service area where the vehicle is scheduled to be stopped in order to take a rest may be set so as to be distant from the position at the current time. When the physiological condition change determining unit determines a change in the physiological condition, the term "determine" means acquiring a change in the current physiological condition and is different from the term "estimate a change in the physiological condition" that means acquiring a change in the future physiological condition.

In the physiological condition estimation device according to the above-mentioned aspect, the variation acquiring unit may count the number of eye-open times that are longer than a predetermined threshold value and the number of eye-open times that are shorter than the predetermined threshold value among the eye-open times acquired by the eye-open time acquiring unit within a predetermined sampling time, thereby acquiring the variation in the eye-open time. As such, it is possible to acquire the variation in the eye-open time from the ratio of the number of long eye-open times and the number of short eye-open times.

Advantageous Effects of Invention

According to the invention, it is possible to prevent an error in the operation of an apparatus, such as a vehicle, and improve the safety of the operation of the apparatus.

BRIEF DESCRIPTION OF DRAWINGS

FIG. 4 is a diagram illustrating the buffer structure of a storage buffer.

FIG. 5 is a diagram illustrating the content of the process of a drowsiness predicting section.

FIG. 6 is a diagram illustrating the content of the process of the drowsiness predicting section.

FIG. 7 is a view illustrating the relationship between the drowsiness level of the examinee and each diagram illustrating the content of the process of the physiological condition estimation device when the physiological condition of the driver, who is the examinee, is estimated.

FIG. 10 is a diagram illustrating an example of the buffer structure of a storage buffer.

FIG. 27 is a diagram illustrating the content of a model application process.

FIG. 29 is a diagram illustrating the value of each constant and the section thereof in the example shown in FIG. 28.

DESCRIPTION OF EMBODIMENTS

Hereinafter, physiological condition estimation devices and vehicle control devices according to exemplary embodiments of the invention will be described in detail with reference to the accompanying drawings.

First Embodiment

Figure 1:
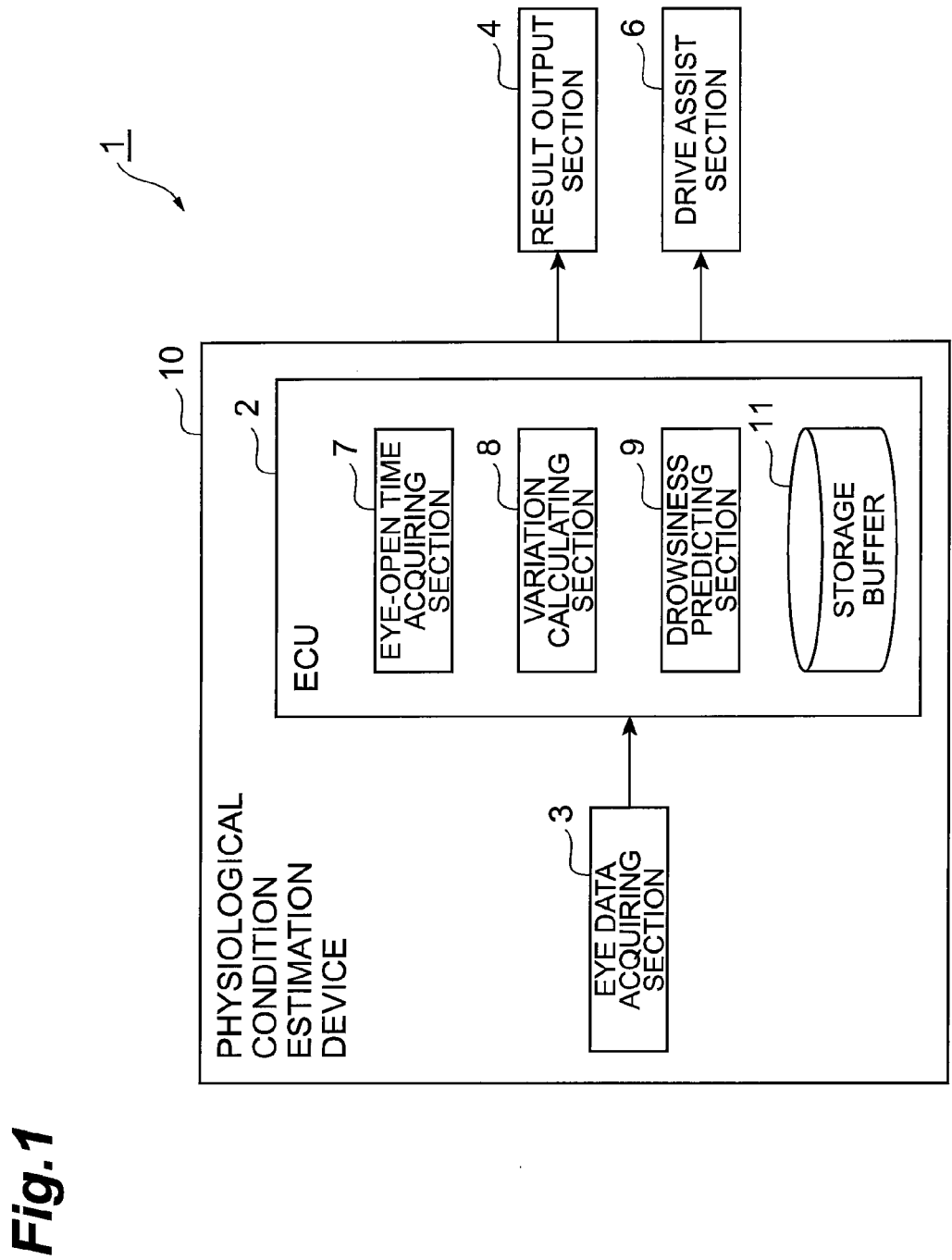
FIG. 1 is a diagram illustrating the block structure of a vehicle control device including a physiological condition estimation device according to a first embodiment.

First, the structure of a physiological condition estimation device 10 and a vehicle control device 1 including the same according to a first embodiment of the invention will be described. FIG. 1 is a diagram illustrating the block structure of the vehicle control device 1 including the physiological condition estimation device 10 according to this embodiment. As shown in FIG. 1, the physiological condition estimation device 10 according to this embodiment includes an ECU (Electronic Control Unit) 2 and an eye data acquiring section 3. In addition, the vehicle control device 1 according to this embodiment includes the physiological condition estimation device 10, a result output section 4, and a drive assist section 6.

The eye data acquiring section 3 of the physiological condition estimation device 10 has a function of acquiring eye data which is a base for acquiring the eye-open time of the driver (object person) of the vehicle. Specifically, the eye data acquiring section 3 consists of, for example, a camera for capturing the image of the eyes of the driver or an eye potential measuring device. The eye data acquiring section 3 has a function of outputting the acquired eye image data or measurement data to the ECU 2.

The ECU 2 of the physiological condition estimation device 10 is an electronic control unit that controls the overall operation of the physiological condition estimation device 10 and includes, for example, a CPU serving as a main component, a ROM, a RAM, an input signal circuit, an output signal circuit, and a power supply circuit. The ECU 2 includes an eye-open time acquiring section (eye-open time acquiring unit) 7, a variation calculating section (variation acquiring unit) 8, a drowsiness predicting section (physiological condition determining unit) 9, and a storage buffer 11.

The eye-open time acquiring section 7 has a function of acquiring the eye-open time of the driver on the basis of the image data or measurement data acquired by the eye data acquiring section 3. Specifically, the eye-open time acquiring section 7 analyzes the image data output from the eye data acquiring section 3 to measure the time for which the eye is opened and the time for which the eye is closed, thereby acquiring the eye-open time. The eye-open time acquiring section 7 has a function of storing the acquired eye-open time data in the storage buffer 11.

The variation calculating section 8 has a function of acquiring a variation in the eye-open time acquired by the eye-open time acquiring section 7. Specifically, the variation calculating section 8 can extract the eye-open time data stored in the storage buffer 11 and perform statistical processing from a standard deviation, a variance, or a histogram, thereby calculating the variation in the eye-open time. For the eye-open time data that is extracted from the storage buffer 11 to be used in the statistical processing, the eye-open time data items within a predetermined unit time width may be extracted, or a predetermined number of eye-open time data items may be extracted from the latest eye-open time data items.

The drowsiness predicting section 9 has a function of determining the physiological condition of the driver on the basis of the variation in the eye-open time calculated by the variation calculating section 8. In this embodiment, drowsiness is determined as the physiological condition that can be determined. However, other physiological conditions, such as an attentiveness reduction or a waking condition, may be determined. As in this embodiment, in determining the drowsiness of the driver, that is, the reduction of the arousal level of the driver, the drowsiness predicting section 9 has a function of determining that it is the condition in which the arousal level of the driver is high when the variation in the eye-open time is determined to be large and it is the condition in which the arousal level of the driver is low when the variation in the eye-open time is determined to be small. The term "low arousal level condition" means a stage before the arousal level is sufficiently reduced to cause an error in the operation of the vehicle (that is, high drowsiness condition), that is, a stage in which a reduction of the arousal level is slight. In this embodiment, this condition is determined in order to prevent the arousal level from being reduced to a value that causes an adverse effect on driving.

The storage buffer 11 has a function of storing the eye-open time data acquired by the eye-open time acquiring section 7. Specifically, as shown in FIG. 4, the storage buffer 11 can store an eye-opening start time, an eye-opening end time, and the eye-open time according to the number of eye blinks. In addition, the storage buffer 11 has a function of outputting the eye-open time data in response to a request from the variation calculating section 8.

The result output section 4 of the vehicle control device 1 has a function of outputting the estimation result of the physiological condition estimation device 10 to the driver. Specifically, the result output section 4 consists of a speaker that can output the estimation result as a voice and a display that can display the estimation result. For example, when the physiological condition estimation device 10 estimates that the driver is in a condition of the arousal level reducing, the result output section 4 may notify the driver of information indicating that drowsiness will occur to have an adverse effect on driving in the future or information indicating that the driver needs to take a rest. Alternatively, when attentiveness is reducing, the result output section 4 may notify the driver of information indicating that the driver needs to pay attention. When the driver wakes up and be in a waking condition, the result output section 4 may notify information indicating that the driver is in the waking condition.

The drive assist section 6 of the vehicle control device 1 has a function of performing a drive assist operation on the basis of the estimation result of the drowsiness predicting section 9. Specifically, the drive assist section 6 consists of, for example, a brake whose sensitivity increases such that the vehicle can be stopped immediately after a brake pedal is pressed or which is capable of forcibly stopping the vehicle, an occupant protection device, a steering wheel capable of increasing steering force in order to prevent unsteady driving, and a driving unit capable of reducing the number of revolutions of the engine.

Figure 2:
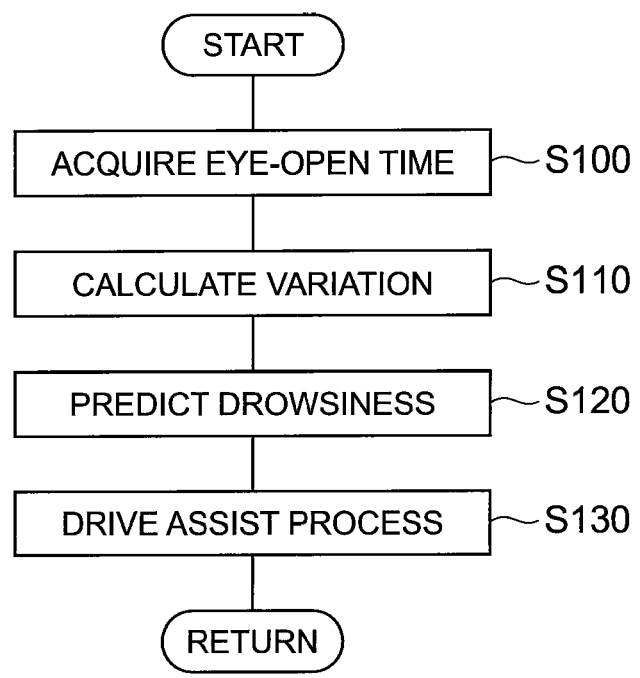
FIG. 2 is a flowchart illustrating an information processing operation of the physiological condition estimation device according to the first embodiment.

Next, the operation of the physiological condition estimation device 10 and the vehicle control device 1 according to this embodiment will be described with reference to FIGS. 2 to 6. FIG. 2 is a flowchart illustrating the information processing operation of the physiological condition estimation device 10 according to this embodiment. The information processing operation shown in FIG. 2 is repeatedly performed by the ECU 2 of the physiological condition estimation device 10 while the vehicle is traveling.

Figure 3:
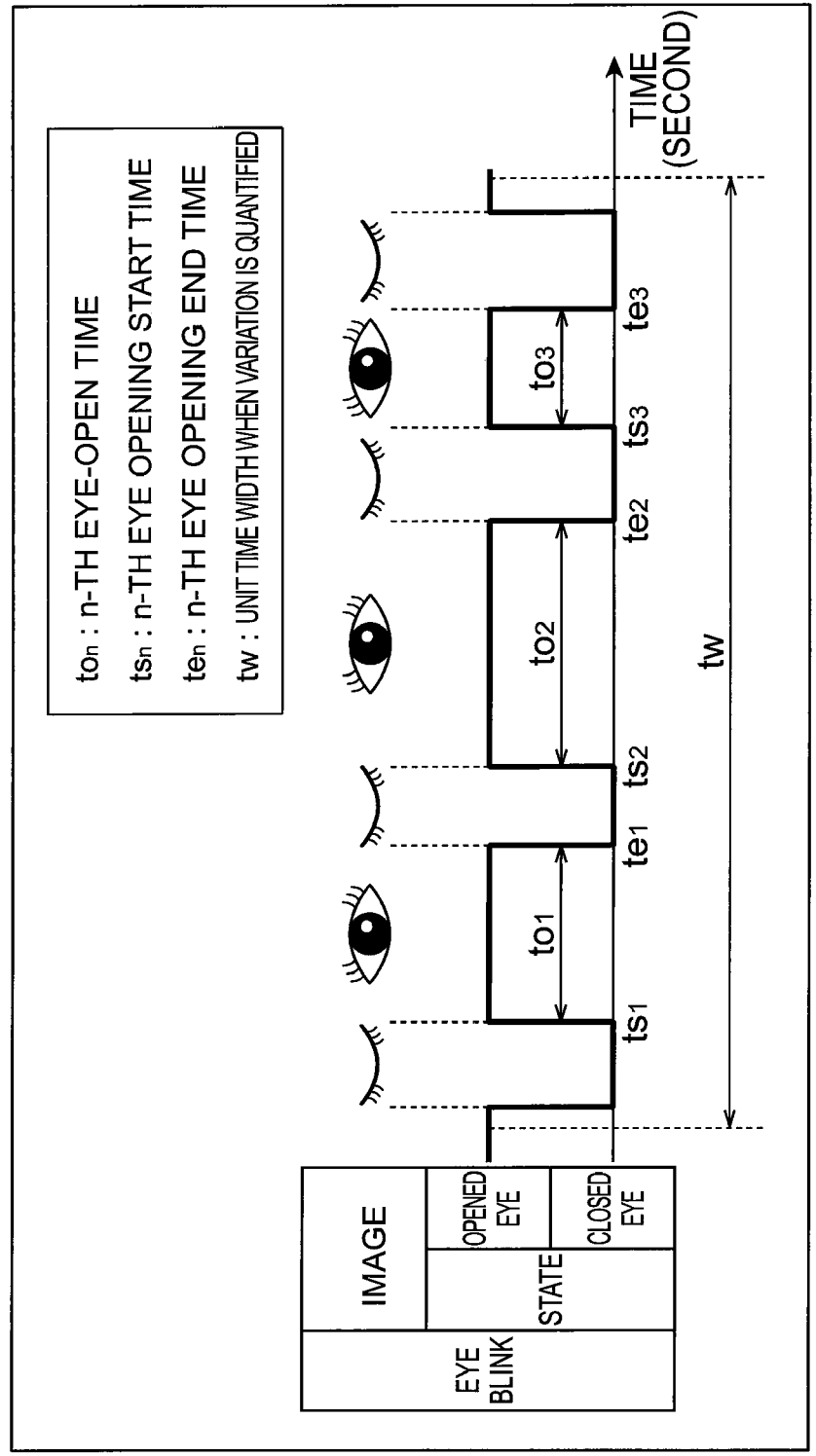
FIG. 3 is a diagram illustrating a method of acquiring an eye-open time in an eye-open time acquiring section, and shows the image of the eye of the driver acquired by an eye data acquiring section and the relationship between the image, the eye-open time, and an eye-closed time.

As shown in FIG. 2, first, the eye-open time acquiring section 7 of the ECU 2 acquires the eye-open time of the driver on the basis of the data acquired by the eye data acquiring section 3 and stores the acquired data in the storage buffer 11 (Step S100). Next, an eye-open time acquiring method of the eye-open time acquiring section 7 will be described in detail with reference to FIG. 3. FIG. 3 is a diagram illustrating the eye-open time acquiring method of the eye-open time acquiring section 7 and shows the image of the eye of the driver acquired by the eye data acquiring section 3 and the relationship between the image, the eye-open time, and the eye-closed time. As shown in FIG. 3, the eye-open time acquiring section 7 analyzes the image of the eye acquired by the eye data acquiring section 3 to determine the eye-open state and the eye-closed state, and measures the eye-open time from an eye-open state start time and an eye-open state end time. Specifically, the time when the eye is first opened from the start of an eye-open time acquiring process is referred to as a first eye-opening start time $ts_1$, the time when the eye is closed thereafter is referred to as a first eye-opening end time $te_1$, and the time between the start time $ts_1$ and the end time $te_1$ is referred to as an eye-open time $to_1$. The time when the eye is opened after the end time $te_1$ is referred to as a second eye-opening start time $ts_2$, the time when the eye is closed thereafter is referred to as a second eye-opening end time $te_2$, and the time between the start time $ts_2$ and the end time $te_2$ is referred to as an eye-open time $to_2$. The time when the eye is opened after the end time $te_2$ is referred to as a third eye-opening start time $ts_3$, the time when the eye is closed thereafter is referred to as a third eye-opening end time $te_3$, and the time between the start time $ts_3$ and the end time $te_3$ is referred to as an eye-open time $to_3$. As such, an n-th eye-open time is referred to as an n-th eye-opening start time $ts_n$, the time when the eye is closed thereafter is referred to as an n-th eye-opening end time $te_n$, the time between the start time $ts_n$ and the end time $te_n$ is referred to as an eye-open time $to_n$. Each data item acquired in this way is stored in the storage buffer 11 in a buffer structure shown in FIG. 4. When a unit time width (time width) during the calculation of the variation is tw, the size of the buffer needs to be more than the unit time width tw. Therefore, the buffer size requirements are represented by $te_n - ts_1 > tw$.

When the eye-open time acquiring process ends, the variation calculating section 8 acquires a variation in the eye-open time on the basis of the eye-open time stored in the storage buffer 11 (Step S110). Specifically, the variation calculating section 8 performs statistical processing on the eye-open time from a standard deviation to calculate a variation in the eye-open time. The variation calculating section 8 acquires a plurality of eye-open time data items for calculating the variation in the eye-open time from the storage buffer 11. In this case, the variation calculating section 8 may acquire the eye-open time data within a predetermined unit time width tw and calculate the variation. That is, when n eye-open time data items are within the unit time width tw, an eye-open time standard deviation (hereinafter, referred to as an eye-open time SD) is calculated on the basis of the eye-open time data $\{to_1, to_2, to_3, \ldots, to_n\}$ stored in the storage buffer 11 by the following Expression 1.

In Expression 1, "n" indicates the total number of acquired eye-open time data items and "I" indicates an eye-open time data number. In addition, "Σ" includes the square of the difference between an i-th eye-opening data item and the average value of n eye-open time data items.

$$SD = \sqrt{\frac{1}{n-1}\sum_{i=1}^{n}(to_i - \overline{to})^2} \, .$$ [Expression 1]

In the above description, the variation calculating section 8 acquires the eye-open time data in the unit time width tw from the storage buffer 11 and calculates the variation. However, instead of this method, a method of acquiring an arbitrary number of eye-open time data items and calculating the variation may be used. For example, when the arbitrary number of eye-open time data items is set to 3, the variation calculating section 8 acquires three latest eye-open time data items $\{to_{n-2}, to_{n-1}, to_n\}$ from the storage buffer and calculates the eye-open time SD on the basis of the eye-opening data items using Expression 1.

After the variation in the eye-open time is calculated, the drowsiness predicting section 9 determines the physiological condition of the driver on the basis of the variation in the eye-open time acquired in Step S110, thereby predicting drowsiness (Step S120). When it is determined in Step S120 that the variation in the eye-open time is large, the drowsiness predicting section 9 determines that it is the condition in which the arousal level of the driver is high. When it is determined that the variation in the eye-open time is small, the drowsiness predicting section 9 determines that it is the condition in which the arousal level of the driver is low.

Next, a detailed method of the physiological condition determining process of the drowsiness predicting section 9 will be described with reference to FIGS. 5 and 6. FIGS. 5 and 6 are diagrams illustrating the content of the process of the drowsiness predicting section 9. First, the drowsiness predicting section 9 plots the eye-open time SD calculated in Step S110 in real time to acquire the diagram shown in FIG. 5(*a*). Then, the drowsiness predicting section 9 calculates the average value of the eye-open time SD for the past x seconds from the current time to smooth FIG. 5(*a*), thereby acquiring the diagram shown in FIG. 5(*b*).

After the eye-open time SD is smoothed, the drowsiness predicting section 9 extracts a position where the average value of the eye-open time SD is less than a predetermined amplitude threshold value Th_a (predetermined threshold value) and acquires the duration time of the position. The duration time means the period from the time when the average value of the eye-open time SD is less than the amplitude threshold value Th_a to the time when the average value of the eye-open time SD is more than the amplitude threshold value Th_a again. Specifically, when a diagram illustrating the average value of the eye-open time SD which is shown at an upper part of FIG. 6(*a*) is obtained, two positions where the average value of the eye-open time SD is less than the amplitude threshold value Th_a are extracted as shown in a lower part of FIG. 6(*a*) and the duration times t1 and t2 of the positions are acquired. When the positions where the average value of the eye-open time SD is less than the threshold value are extracted, the positions where the duration time is more than a predetermined time threshold value Th_t among the extracted positions are extracted. Specifically, when the extraction result shown at the lower part of FIG. 6(*a*) is obtained, the duration time t1 is less than the time threshold value Th_t, and the duration time t2 is more than the time threshold value Th_t, only the position of the duration time t2 is extracted, as shown in FIG. 6(*b*).

By the above-mentioned process, when the state in which the duration time for which the average value of the eye-open time SD is less than the amplitude threshold value Th_a is equal to or less than the time threshold value Th_t is maintained, the drowsiness predicting section 9 determines that the variation in the eye-open time is large and it is the condition in which the arousal level of the driver is high. When the position where the duration time for which the average value of the eye-open time SD is less than the amplitude threshold value Th_a is more than the time threshold value Th_t is extracted, the drowsiness predicting section 9 determines that the variation in the eye-open time is small and it is the condition in which the arousal level of the driver is low. In this way, the drowsiness predicting section 9 can predict the drowsiness of the driver. Steps S100 to S120 are repeatedly performed until the arousal level of the driver is determined to be low. When the low arousal level condition is determined, the process proceeds to the next Step S130.

When the drowsiness predicting section 9 determines that it is the condition in which the arousal level of the driver is low (that is, when drowsiness is predicted), the ECU 2 outputs a control signal to the result output section 4 or the drive assist section 6 to perform a drive assist process (Step S130). Specifically, the result output section 4 may output a voice or display an image to inform the driver that drowsiness will occur in the future and prompt the driver to take a rest. In addition, the drive assist section 6 is controlled to perform the following operation: an operation of increasing boost pressure such that the vehicle can be stopped immediately after the brake pedal is pressed; an operation of evacuating the vehicle to a safe position and forcibly operating the brake such that the driver takes a rest with reference to map information of a navigation apparatus; an operation of rolling up a seatbelt so as to facilitate the operation of an occupant protection device, such as the operation of an occupant protection bag or the movement of a headrest for reducing a whiplash injury; an operation of detecting the lane with a camera and giving steering force such that lane departure does not occur or the vehicle keeps its lane; an operation of detecting the distance from the vehicle in front with a millimeter-wave radar or a laser beam and maintaining a predetermined inter-vehicle distance, or setting the inter-vehicle distance to a large value; an operation of monitoring a surrounding obstacle with a camera image and assisting an avoiding operation using the brake or the steering wheel; or an operation of reducing the number of revolutions of the engine. When the drive assist process ends, the control process shown in FIG. 2 ends. Then, the process starts again from Step S100.

In the method of detecting the physiological condition according to the related art, it is possible to detect a reduction in the arousal level to a value that affects the operation of the vehicle, but it is difficult to detect a slight reduction in the arousal level before the arousal level affects the operation of the vehicle. Therefore, it is difficult to prevent an error in the driving of the vehicle. However, according to the physiological condition estimation device 10 of this embodiment, the eye-open time of the driver is acquired and the physiological condition of the driver is determined on the basis of a variation in the eye-open time. Therefore, it is possible to detect a slight reduction in the arousal level and thus estimate preliminarily a large reduction in the arousal level to a value that will cause an error in the driving of the vehicle in the future. In particular, the vehicle control device 1 according to this embodiment controls the vehicle on the basis of the variation in the eye-open time of the driver to support driving before the stage in which an error occurs in the driving of the vehicle. In this way, it is possible to improve the operation safety of an apparatus, such as a vehicle.

Next, an example of the physiological condition estimation device 10 according to this embodiment will be described with reference to FIG. 7. FIG. 7 shows the relationship between diagrams illustrating the content of the process of the physiological condition estimation device 10 when the physiological condition of the driver, who is an examinee, is estimated and the drowsiness level of the examinee. FIG. 7($a$) is a diagram illustrating an eye-open time standard deviation, FIG. 7($b$) is a diagram illustrating the average value of the eye-open time standard deviation, that is, the smoothing of the eye-open time standard deviation, FIG. 7($c$) is a diagram illustrating the duration time for which the average value of the eye-open time standard deviation is less than the amplitude threshold value Th_a in FIG. 7($b$), FIG. 7($d$) is a diagram illustrating the extracted position where the duration time for which the average value of the eye-open time standard deviation is less than the threshold value is more than the time threshold value Th_t in FIG. 7($c$), and FIG. 7($e$) is a diagram illustrating the drowsiness level reported by the examinee. As described above, in FIG. 6($a$), the duration times (t1 and t2) are simply measured for each position where the average value of the eye-open time standard deviation is less than the amplitude threshold value Th_a. However, in FIG. 7($c$), in order to exclude the influence of noise on measurement, the physiological condition is determined using the diagram that is measured by adding the duration time for which the average value of the eye-open time standard deviation is less than the threshold value. In this example, when the diagram of the eye-open time standard deviation shown in FIG. 7($a$) is obtained, as shown in FIG. 7($c$), only the position where the duration time is more than the time threshold value Th_t appears in the vicinity of 700 seconds after the start of measurement. In this case, the position is detected as shown in FIG. 7($d$). In this way, it is possible to determine that the arousal level is low in the vicinity of 700 seconds. When the relationship between this result and the drowsiness level of the examinee is verified, as shown in FIG. 7($e$), the arousal level is rapidly reduced at a position P2 that is a few minutes after the position P1 where the arousal level is determined to be low. Finally, the driver is unconscious. The arousal level is so low that the driving of the vehicle is hindered at the position P2. The physiological condition estimation device 10 can predict this condition a few minutes previously.

Second Embodiment

Next, a physiological condition estimation device 110 and a vehicle control device 100 according to a second embodiment of the invention will be described with reference to FIGS. 8 and 9. The physiological condition estimation device 110 and the vehicle control device 100 according to the second embodiment are mainly different from the physiological condition estimation device 10 and the vehicle control device 1 according to the first embodiment in that the unit time width for calculating the variation in the eye-open time is not set to a fixed constant, but is set so as to be most suitable for each driver. In the first embodiment, the predetermined unit time width is tw. However, in the second embodiment, the unit time width that is set so as to be most suitable for each driver is represented by W.

Figure 8:
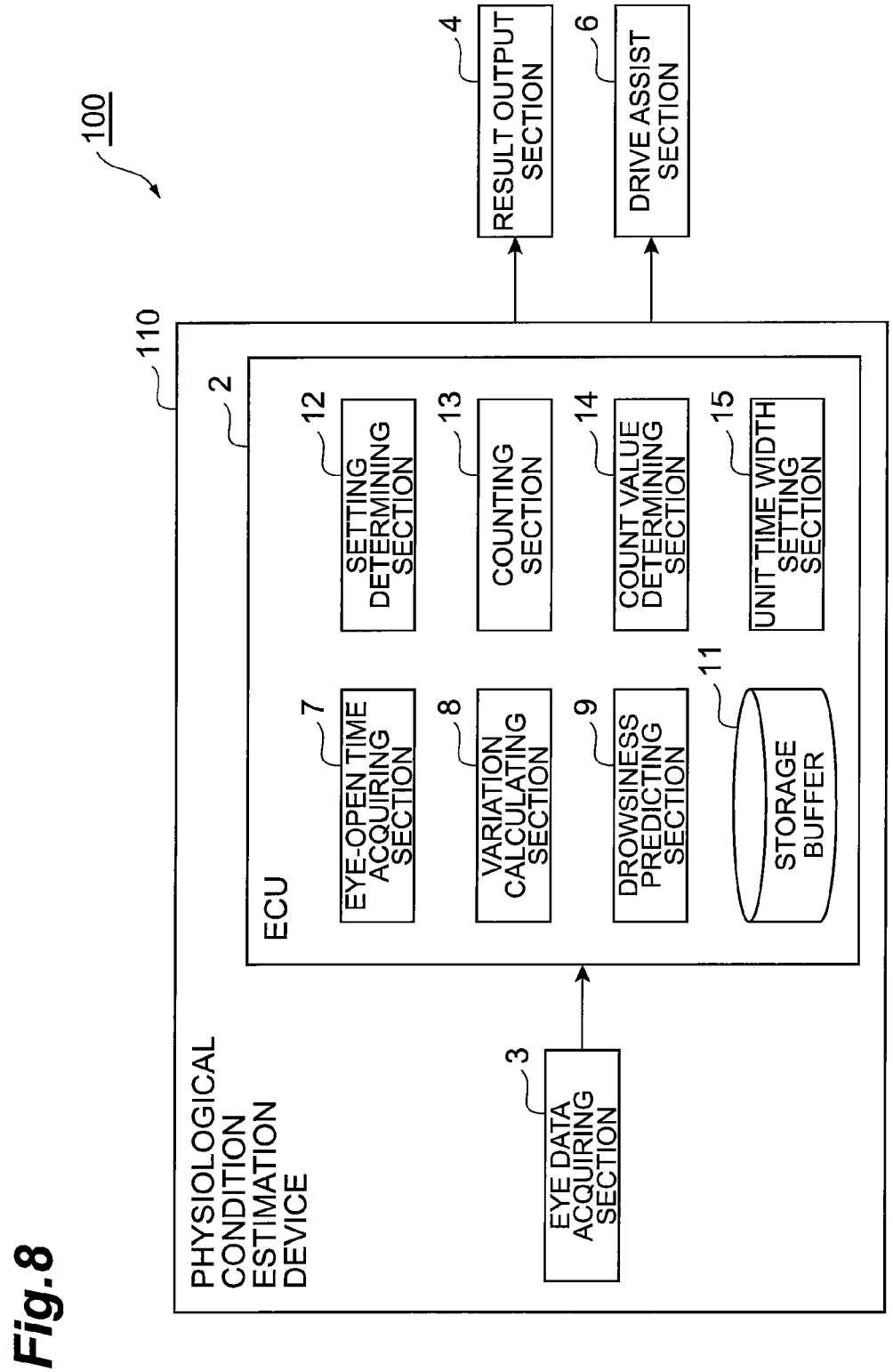
FIG. 8 is a diagram illustrating the block structure of a physiological condition estimation device and a vehicle control device according to a second embodiment.

FIG. 8 is a diagram illustrating the block structure of the physiological condition estimation device 110 and the vehicle control device 100 according to the second embodiment. As shown in FIG. 8, an ECU 2 of the physiological condition estimation device 110 includes a setting determining section 12, a counting section 13, a count value determining section 14, and a unit time width setting section (time width setting unit) 15. The other structures are the same as those of the physiological condition estimation device 10 and the vehicle control device 1 according to the first embodiment.

The setting determining section 12 has a function of determining whether the unit time width for calculating the variation in the eye-open time has been set. The counting section 13 has a function of counting the number of eye-open time data items stored in the storage buffer 11. The count value determining section 14 has a function of determining whether the number of eye-open time data items counted by the counting section 13 is a value required to set the unit time width W. The unit time width setting section 15 has a function of setting the unit time width W suitable for each driver.

Next, the operation of the physiological condition estimation device 110 and the vehicle control device 100 according to this embodiment will be described with reference to FIG. 9. FIG. 9 is a flowchart illustrating an information processing operation of the physiological condition estimation device 110 according to this embodiment. The information processing operation shown in FIG. 9 is repeatedly performed by the ECU 2 of the physiological condition estimation device 10 while the vehicle is traveling from the start of operation.

Figure 9:
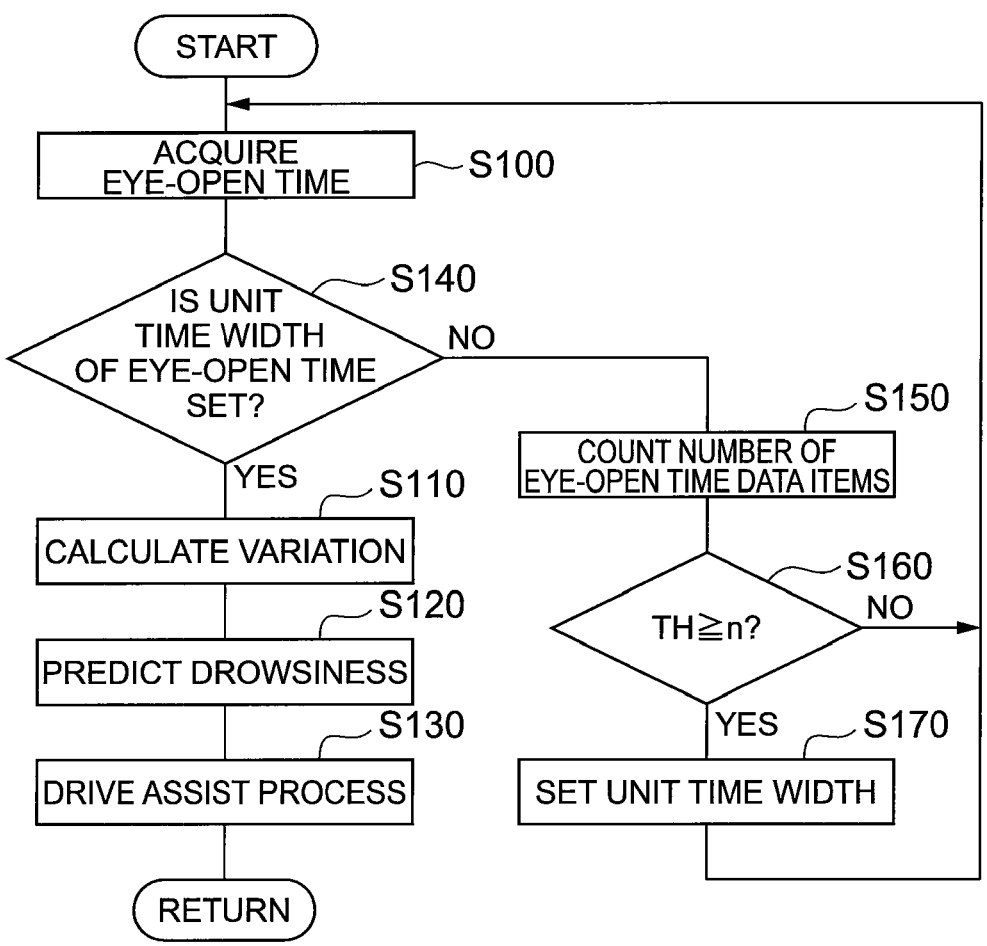
FIG. 9 is a flowchart illustrating an information processing operation of the physiological condition estimation device according to the second embodiment.

As shown in FIG. 9, the eye-open time acquiring section 7 acquires the eye-open time of the driver and stores the acquired eye-open time data in the storage buffer 11 (Step S100). In Step S100, the same process as that in Step S100 shown in FIG. 2 is performed. Then, the setting determining section 12 determines whether the unit time width W of the eye-open time has been set (Step S140). First, in the stage in which the driving of the vehicle starts, the unit time width W for calculating the variation in Step S110 has not been set. Therefore, in the initial stage of driving, it is determined that the unit time width of the eye-open time has not been set. Once the eye-open time is set, it is determined in the subsequent process that the unit time width W of the eye-open time has been set, and the process proceeds to a variation calculating step (Step S110).

When it is determined in Step S140 that the unit time width W has not been set, the counting section 13 counts the number of eye-open time data items (Step S150). In Step S150, the number of eye-open time data items stored in the storage buffer 11 during the period from the initial stage of the start of driving to the current time is counted. For example, when the data shown in FIG. 10 is stored in the storage buffer, the number of data items counted by the counting section 13 is 6. When the number of eye-open time data items is counted, the count value determining section 14 determines whether the number of data items satisfies number requirements for setting the unit time width W (Step S160). Specifically, a number requirement TH for setting the unit time width W is predetermined. When the number of data items counted in Step S150 is n and TH n is satisfied, it is determined that the requirements are satisfied. When TH<n is satisfied, it is determined that the requirements are not satisfied. The number requirement TH may be set to any value. It is preferable that the number requirement TH be three or more (TH≥3). In Step S160, when TH<n is satisfied and it is determined that the requirements are not satisfied, the process returns to S100 and the eye-open time is acquired again such that a necessary number of data items is obtained.

When it is determined in Step S160 that TH≥n is satisfied and the requirements are satisfied, the unit time width setting section 15 sets the unit time width W (Step S170). In Step S170, specifically, the standard deviation (hereinafter, referred to as SD) and the average value (hereinafter, referred to as M) of TH eye-open time data items in the storage buffer 11 are calculated. Then, the calculated values are substituted into the following Expression 2 to calculate the unit time width W. For example, when TH=6 and the values shown in FIG. 10 are used to calculate the unit time width W, the average value M is 9.8 and the standard deviation SD is 3.8. Therefore, the unit time width W is 21.2.

$$W = M + (3 \times SD)$$ [Expression 2]

When the unit time width W is set in Step S170, the process returns to Step S100 and Steps S100 and S140 are performed again. Since the unit time width W is set, it is determined in Step S140 that the unit time width W has been set and the process proceeds to a variation calculating step (S110). The variation calculating section 8 acquires the latest eye-open time data in the unit time width W set in Step S170 from the storage buffer 11 and calculates the variation. Then, the drowsiness predicting process (S120) and the drive assist process (S130) are performed. In the calculation of the variation and Steps S120 and S130, the same process as that in the first embodiment is performed. When the drive assist process ends, the control process shown in FIG. 2 ends. Then, the process starts again from Step S100.

As described above, the physiological condition estimation device 110 according to this embodiment includes the unit time width setting section 15 that can set the unit time width W required for statistical processing in the variation calculating section 8 on the basis of a plurality of eye-open time data items acquired by the eye-open time acquiring section 7. Therefore, it is possible to calculate the variation with the unit time width that is suitable for each driver. When the unit time width for calculating the variation is set to a constant value, it is difficult to respond to the difference between the eye-open times of the individual drivers, and the accuracy of estimating the physiological condition of a specific driver is likely to be reduced. However, according to the physiological condition estimation device 110 of this embodiment, it is possible to estimate the physiological condition of everybody with high accuracy, regardless of the difference between the individual drivers.

Third Embodiment

Next, a physiological condition estimation device 210 and a vehicle control device 200 according to a third embodiment of the invention will be described with reference to FIG. 11 and FIG. 12. The physiological condition estimation device 210 and the vehicle control device 200 according to the third embodiment are mainly different from the physiological condition estimation device 10 and the vehicle control device 1 according to the first embodiment in that the drowsiness predicting section 9 does not simply set to the amplitude threshold value (which is represented by Th_a in the first embodiment) used to estimate the physiological condition to a constant value, but sets the amplitude threshold value so as to be most suitable for each driver. In addition, in the first embodiment, the predetermined amplitude threshold value is Th_a. However, in the third embodiment, the amplitude threshold value is set to a value that is the most suitable for each driver at the current time t0 and is represented by TH(t0).

Figure 11:
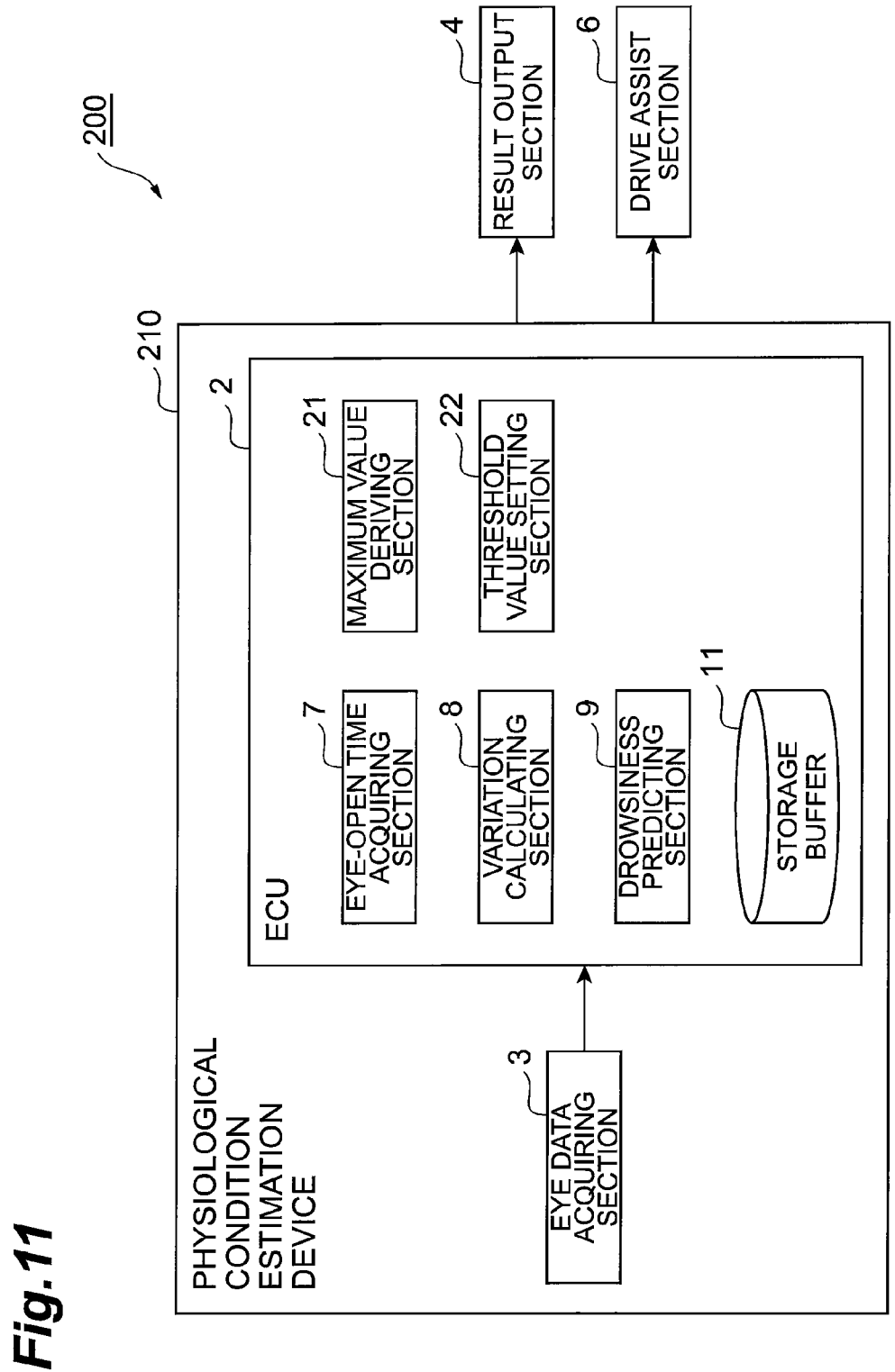
FIG. 11 is a diagram illustrating the block structure of a physiological condition estimation device and a vehicle control device according to a third embodiment.

FIG. 11 is a diagram illustrating the block structure of the physiological condition estimation device 210 and the vehicle control device 200 according to the third embodiment. As shown in FIG. 11, an ECU 2 of the physiological condition estimation device 210 includes a maximum value calculating section (maximum value deriving unit) 21 and a threshold value setting section (threshold value setting unit) 22. The other structures are the same as those of the physiological condition estimation device 10 and the vehicle control device 1 according to the first embodiment.

The maximum value deriving section 21 has a function of deriving the maximum value of a variation in an eye-open time and updates the maximum value. Specifically, the maximum value deriving section 21 derives the maximum value of the variation in the eye-open time on the basis of the standard deviation or variance of the eye-open time from the start of driving to the present time which is calculated by the variation calculating section 8 and updates the existing maximum value. The threshold value setting section 22 has a function of setting the amplitude threshold value TH(t0) on the basis of the maximum value of the variation derived by the maximum value deriving section 21. Specifically, the amplitude threshold value TH(t0) can be defined as the rate of reduction of the variation in the eye-open time from the maximum value.

Next, the operation of the physiological condition estimation device 210 and the vehicle control device 200 according to this embodiment will be described with reference to FIG. 12. FIG. 12 is a flowchart illustrating an information processing operation of the physiological condition estimation device 210 according to this embodiment. The information processing operation shown in FIG. 12 is repeatedly performed by the ECU 2 of the physiological condition estimation device 210 while the vehicle is traveling from the start of driving.

Figure 12:
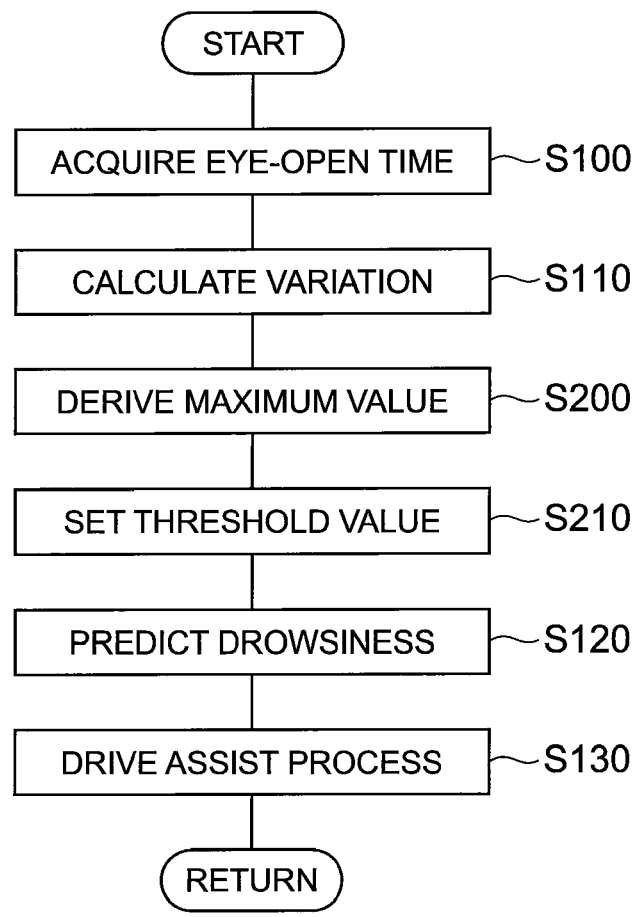
FIG. 12 is a flowchart illustrating an information processing operation of the physiological condition estimation device according to the third embodiment.
Figure 13:
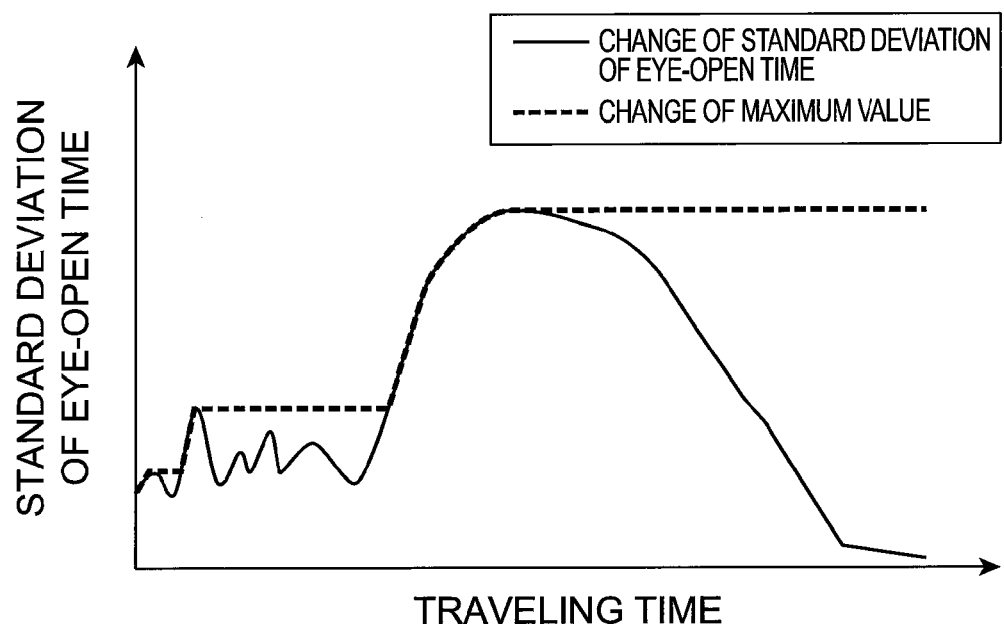
FIG. 13 is a diagram illustrating the process of a maximum value deriving section.

As shown in FIG. 12, the eye-open time acquiring section 7 stores the eye-open time of the driver and stores the acquired eye-open time data in the storage buffer 11 (Step S100). Then, the variation calculating section 8 calculates a variation in the eye-open time, that is, the standard deviation of the eye-open time on the basis of the eye-open time data (Step S110). In Steps S100 and S110, the same process as that in Steps S100 and S110 of FIG. 2 is performed. Then, the maximum value deriving section 21 derives the maximum value of the standard deviation calculated in Step S110 (Step S200). In Step S200, specifically, as shown in FIG. 13, the maximum value of the standard deviation of the eye-open time from the start of driving to the current time is derived. When a value more than the existing maximum value is derived, the maximum value is updated with a new value. Therefore, the maximum value varies over time. That is, when a large peak occurs once, the peak value is the maximum value and the maximum value is maintained for a predetermined period of time. When a peak more than the existing peak occurs, the peak value is updated with a new maximum value and the maximum value is maintained for a predetermined period of time.

After the maximum value at the current time is derived, the threshold value setting section 22 sets the amplitude threshold value TH(t0) at the current time (Step S210). Specifically, the maximum value $SD_{max}$ of the standard deviation of the eye-open time may be substituted into Expression 3 to calculate the amplitude threshold value TH(t0). In Expression 3, any value may be set as a coefficient A. It is preferable that the coefficient A be set to around 0.5.

$$TH(t0)=SD_{max}-(A\times SD_{max}) \quad \text{[Expression 3]}$$

Figure 14:
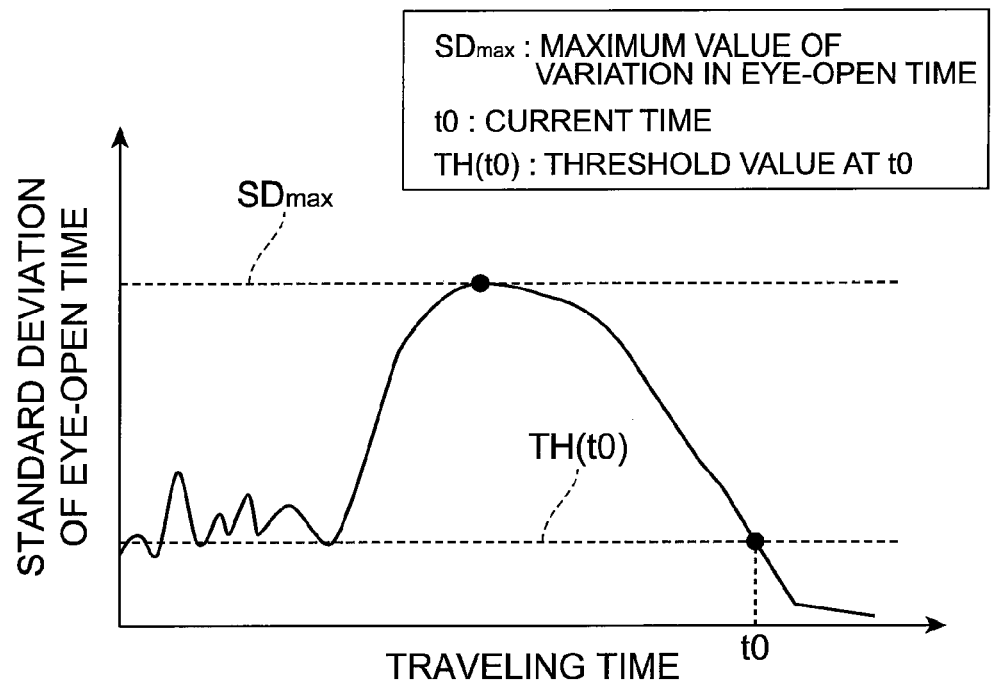
FIG. 14 is a diagram illustrating the process of a threshold value setting section.

FIG. 14 shows an example of the relationship between the amplitude threshold value TH(t0) obtained in this way and the standard deviation of the eye-open time. In the example shown in FIG. 14, the variation in the eye-open time is the maximum in the stage before the current time t0 and is then reduced so as to be equal to the amplitude threshold value TH(t0) at the current time t0. After the current time t0, the variation is maintained to be less than the amplitude threshold value TH(t0) (the maximum value $SD_{max}$ is constant).

In Step S210, when the amplitude threshold value TH (t0) is set, the drowsiness predicting section 9 performs a physiological condition estimating process using the amplitude threshold value TH(t0) (S120). Step S120 is the same as that in the first embodiment except that the amplitude threshold value Th_a is replaced with the amplitude threshold value TH(t0). When the physiological condition estimating process ends, the drive assist process (S130) is performed. In Step S130, the same process as that in the first embodiment is performed. When the drive assist process ends, the control process shown in FIG. 2 ends. Then, the process starts again from Step S100.

As described above, in the physiological condition estimation device 210 according to this embodiment, it is possible to update the maximum value $SD_{max}$ of the variation in the eye-open time and set the amplitude threshold value TH(t0) on the basis of the updated maximum value $SD_{max}$. For example, when the eye-open time of the driver is long, the variation in the eye-open time tends to increase. Therefore, when the amplitude threshold value is set to a constant value according to the driver with a short eye-open time, the variation in the eye-open time of the driver with a long eye-open time does not reach the amplitude threshold value, which makes it difficult to determine a reduction in the arousal level. On the other hand, when the amplitude threshold value is set according to the driver with a long eye-open time, a reduction in the arousal level of the driver with a short eye-open time is likely to be unnecessarily determined. Therefore, when the amplitude threshold value is constantly set, it is difficult to respond to the difference between the variations in the eye-open time of the individual drivers and thus estimate the physiological condition of everybody with high accuracy. However, the physiological condition estimation device according to this embodiment sets the amplitude threshold value TH(t0) on the basis of the maximum value of the variation in the eye-open time. Therefore, it is possible to respond to the difference between the variations in the eye-open time of the individual drivers and thus estimate the physiological condition of everybody with high accuracy. In addition, the maximum value for setting the amplitude threshold value TH(t0) is updated over time and the updated maximum value is set. Therefore, for example, even when the driver is in drowsy condition during the start of driving and the arousal level of the driver increases during driving, it is possible to accurately estimate the physiological condition of the driver according to the unique variation characteristics of the driver.

Fourth Embodiment

Next, a physiological condition estimation device 310 and a vehicle control device 300 according to a fourth embodiment of the invention will be described with reference to FIG. 15. The physiological condition estimation device 310 and the vehicle control device 300 according to the fourth embodiment are mainly different from the physiological condition estimation device 10 and the vehicle control device 1 according to the first embodiment in that an attentiveness-reduced condition is determined. In this embodiment, the term "attentiveness-reduced condition" means that the driver is in an absentminded condition. The term "attentiveness-reduced condition" is a stage before the "low arousal level condition" in the first embodiment.

Figure 15:
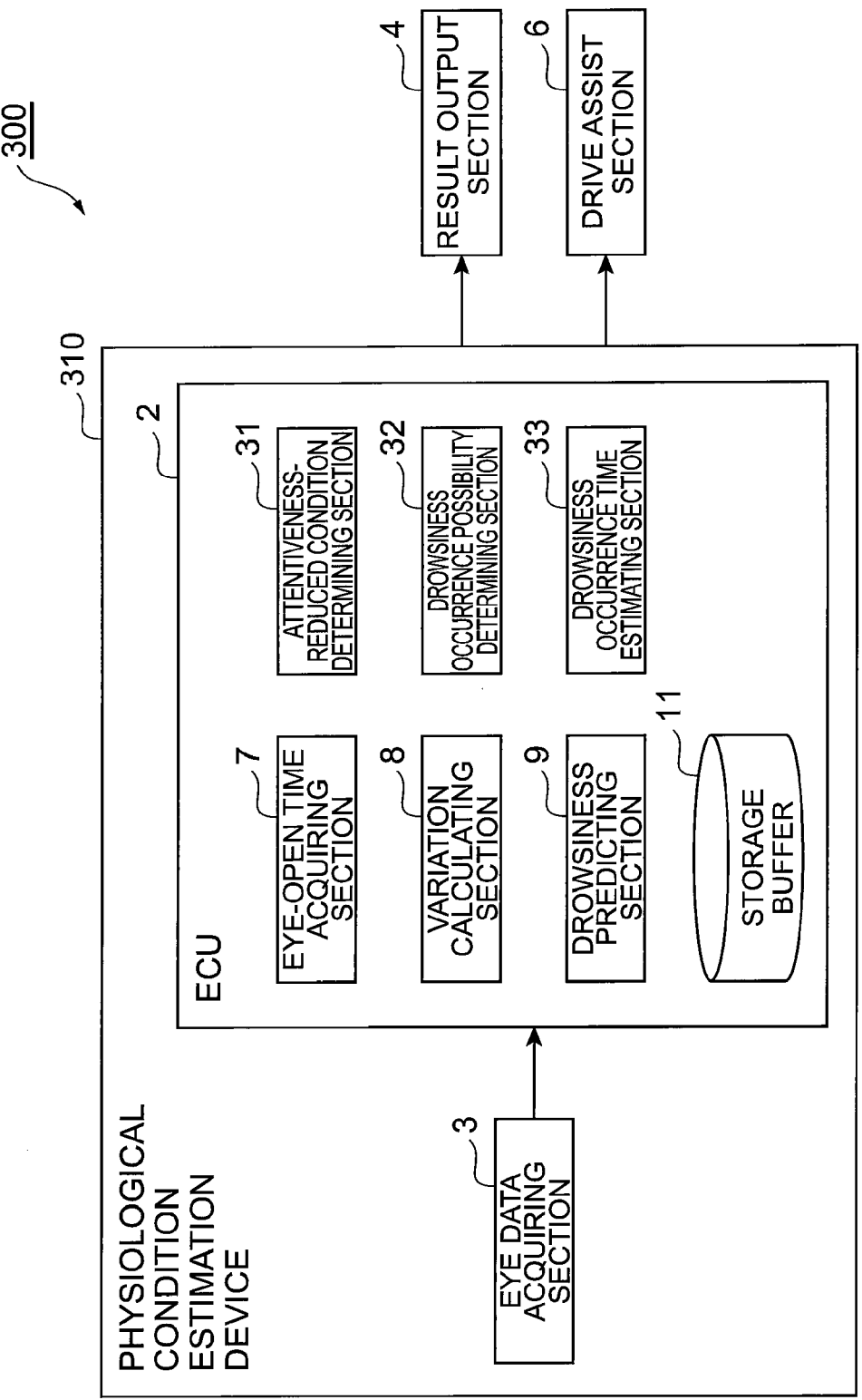
FIG. 15 is a diagram illustrating the block structure of a physiological condition estimation device and a vehicle control device according to a fourth embodiment.

FIG. 15 is a diagram illustrating the block structure of the physiological condition estimation device 310 and the vehicle control device 300 according to the fourth embodiment. As shown in FIG. 15, an ECU 2 of the physiological condition estimation device 310 includes an attentiveness-reduced condition determining section (physiological condition determining unit) 31, a drowsiness occurrence possibility determining section (drowsiness occurrence possibility determining unit) 32, and a drowsiness occurrence time estimating section (drowsiness occurrence estimating unit) 33. The other structures are the same as those of the physiological condition estimation device 10 and the vehicle control device 1 according to the first embodiment.

The attentiveness-reduced condition determining section 31 has a function of determining whether the attentiveness of the driver is reduced. The attentiveness-reduced condition determining section 31 has a function of detecting the attentiveness-reduced condition of the driver on the basis of the determination result. Specifically, the attentiveness-reduced condition determining section 31 may determine whether the attentiveness of the driver is reduced on the basis of an increase in the variation in the eye-open time. The attentiveness-reduced condition determining section 31 compares the variation in the eye-open time with a predetermined threshold value to perform the determination process. A detailed determination method will be described below.

The drowsiness occurrence possibility determining section 32 has a function of determining whether there is a possibility of the driver reaching a drowsy condition. The drowsiness occurrence possibility determining section 32 sets an approximate straight line to the variation in the eye-open time and performs the determination process on the basis of the gradient of the approximate straight line. The drowsiness occurrence possibility determining section 32 sets an approximate straight line to a variation in the eye-open time within a predetermined time width. A detailed determination method will be described below.

The drowsiness occurrence time estimating section 33 has a function of estimating the time until the driver will reach the drowsy condition. The "drowsy condition" that can be predicted in this embodiment is a condition in which the arousal level is reduced and indicates the "low arousal level condition" or the subsequent conditions in the first embodiment. The drowsiness occurrence time estimating section 33 can estimate the time using the approximate straight line set by the drowsiness occurrence possibility determining section 32. The drowsiness occurrence time estimating section 33 extends the approximate straight line and estimates the time when the approximate straight line will reach a predetermined threshold value as the time when drowsiness occurs.

Figure 16:
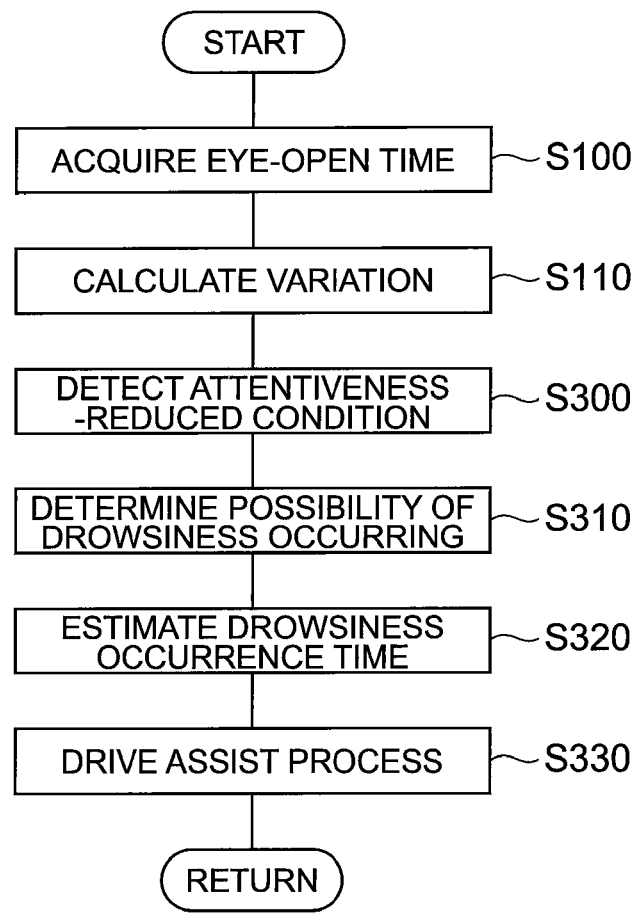
FIG. 16 is a flowchart illustrating an information processing operation of the physiological condition estimation device according to the fourth embodiment.

Next, the operation of the physiological condition estimation device 310 and the vehicle control device 300 according to this embodiment will be described with reference to FIG. 16. FIG. 16 is a flowchart illustrating an information processing operation of the physiological condition estimation device 310 according to this embodiment. The information processing operation shown in FIG. 16 is repeatedly performed by the ECU 2 of the physiological condition estimation device 310 while the vehicle is traveling from the start of driving.

As shown in FIG. 16, the eye-open time acquiring section 7 acquires the eye-open time of the driver and stores the acquired eye-open time data in the storage buffer 11 (Step S100). Then, the variation calculating section 8 calculates a variation in the eye-open time, that is, the standard deviation of the eye-open time on the basis of the eye-open time data (Step S110). In Steps S100 and S110, the same process as that in Steps S100 and S110 shown in FIG. 2 is performed.

Figure 17:
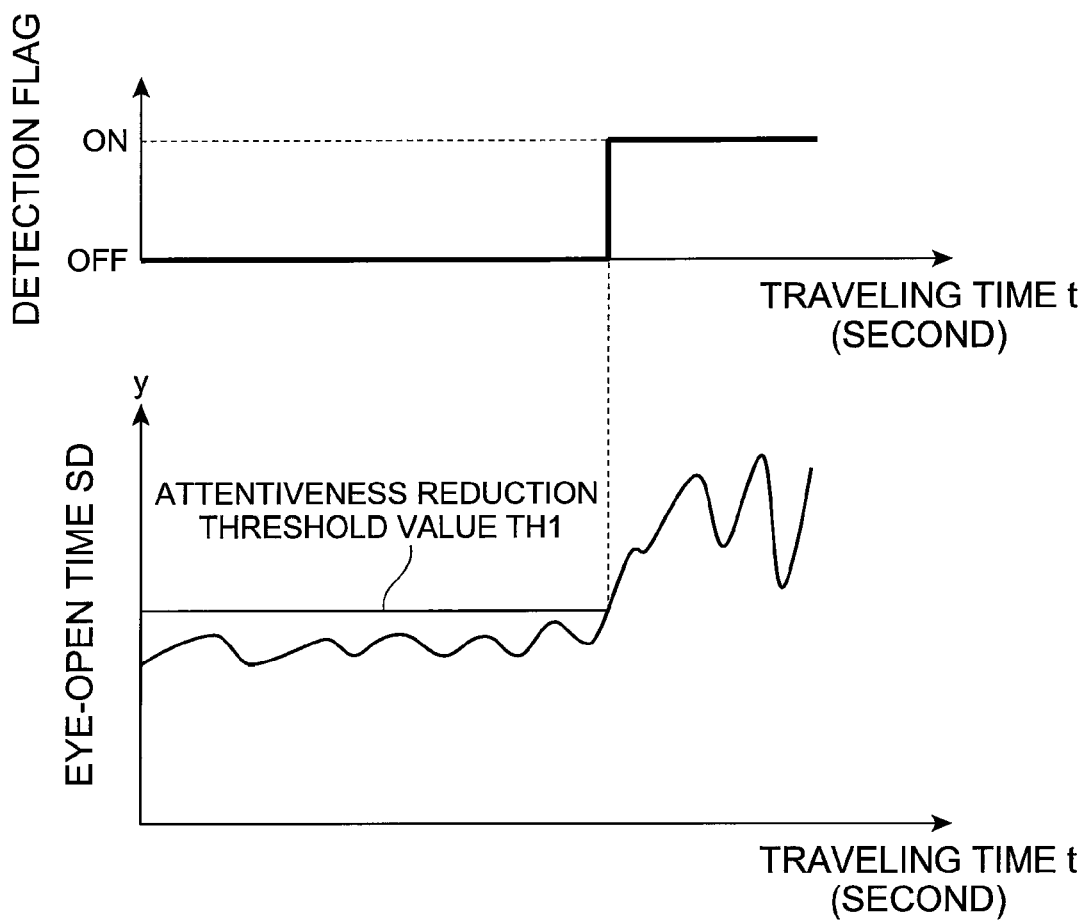
FIG. 17 is a diagram illustrating the content of the process of an attentiveness-reduced condition determining section.

The attentiveness-reduced condition determining section 31 detects the attentiveness-reduced condition of the driver (Step S300). In step S300, the attentiveness-reduced condition determining section 31 determines whether the attentiveness of the driver is reduced on the basis of an increase in the variation in the eye-open time. The attentiveness-reduced condition determining section 31 detects the attentiveness-reduced condition at the time when attentiveness is determined to be reduced. The attentiveness-reduced condition determining section 31 compares the variation in the eye-open time with an attentiveness reduction threshold value TH1. Specifically, the attentiveness-reduced condition determining section 31 determines whether the conditions represented by Expression 4 are established and detects the attentiveness-reduced condition at the time when Expression 4 is established. SD(t) indicates a variation in the eye-open time at a predetermined time t. As shown in FIG. 17, when the variation in the eye-open time is equal to or more than the attentiveness reduction threshold value TH1, the attentiveness-reduced condition determining section 31 turns on a detection flag of the attentiveness-reduced condition.

$$SD(t) \geq TH1 \quad \text{[Expression 4]}$$

The attentiveness reduction threshold value TH1 is calculated by Expression 5. In Expression 5, MEAN_SD is the average value of a variation SD(t) in the eye-open time from the start of driving to an arbitrary time tn. N is a predetermined coefficient. Any value may be set as the coefficient N. For example, the coefficient N may be set to 3 or 5, which will be described below. STDEV_SD is the standard deviation of the variation SD(t) in the eye-open time from the start of driving to an arbitrary time tn.

$$TH1 = \text{MEAN\_SD} + N \times \text{STDEV\_SD} \quad \text{[Expression 5]}$$

Figure 18:
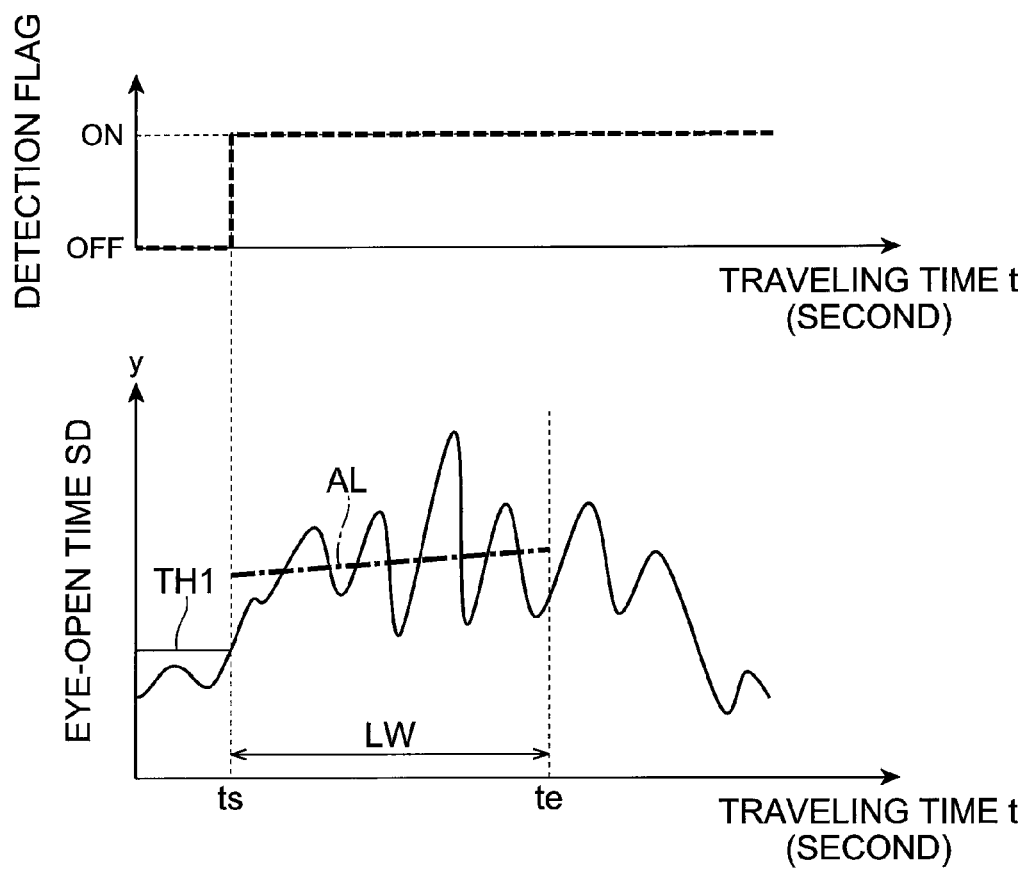
FIG. 18 is a diagram illustrating the content of the process of a drowsiness occurrence possibility determining section.

Next, the drowsiness occurrence possibility determining section 32 determines whether there is a possibility of the driver reaching a drowsy condition (Step S310). As shown in FIG. 18, the drowsiness occurrence possibility determining section 32 sets an approximate straight line AL to the variation in the eye-open time and performs the determination process on the basis of the gradient of the approximate straight line AL. The approximate straight line AL is set to the variation in the eye-open time in an application section. The application section is determined on the basis of the time when a reduction in attentiveness is detected. Specifically, the drowsiness occurrence possibility determining section 32 sets the time when the flag for detecting a reduction in attentiveness is turned on in Step S300 as the start time ts of the application section. The drowsiness occurrence possibility determining section 32 sets the time after the time width LW of the application section has elapsed from the start time ts as the end time te of the application section. When the variation in the eye-open time is not acquired during the entire section from the start time ts to the end time te, the drowsiness occurrence possibility determining section 32 waits until the acquisition is completed. The drowsiness occurrence possibility determining section 32 sets the approximate straight line AL to the variation in the eye-open time in the section from the start time ts to the end time te. A method of setting the approximate straight line AL is not particularly limited. Any method may be used as long as a straight line can be acquired. For example, a least-squares method may be used as an approximating method. The approximate straight line AL is represented by Expression 6. In Expression 6, the gradient of the approximate straight line is A. The gradient A indicates the amount of change of the variation in the eye-open time with respect to time. When the gradient A of the approximate straight line is negative (A<0), the drowsiness occurrence possibility determining section 32 determines that there is a possibility of the driver reaching a drowsy condition. In the example shown in FIG. 18, the gradient of the approximate straight line AL is a positive value. Therefore, the drowsiness occurrence possibility determining section 32 determines that there is no possibility of drowsiness occurring. When it is determined that there is "no possibility of drowsiness occurring", the drowsiness occurrence possibility determining section 32 shifts the start time ts and the end time te over time with the time width LW being estimated. In addition, the drowsiness occurrence possibility determining section 32 repeats the determination process of Step S310 until it is determined that there is a possibility of drowsiness occurring. The time when the drowsiness occurrence possibility determining section 32 determines that there is a "possibility of drowsiness occurring" is identical to the end time te. The value of the time width LW of the application section is not particularly limited, but an arbitrary time may be set as the time width LW. The time width LW may be set to, for example, 3 minutes. In the case of a person requiring a short time to fall asleep, the shortest time to fall asleep is about 3 minutes (for example, due to sleep disorders). Therefore, when the time width LW is set to 3 minutes, the drowsiness occurrence possibility determining section 32 can rapidly determine the possibility of drowsiness occurring for any driver.

$$y = At + B \quad \text{[Expression 6]}$$

Figure 19:
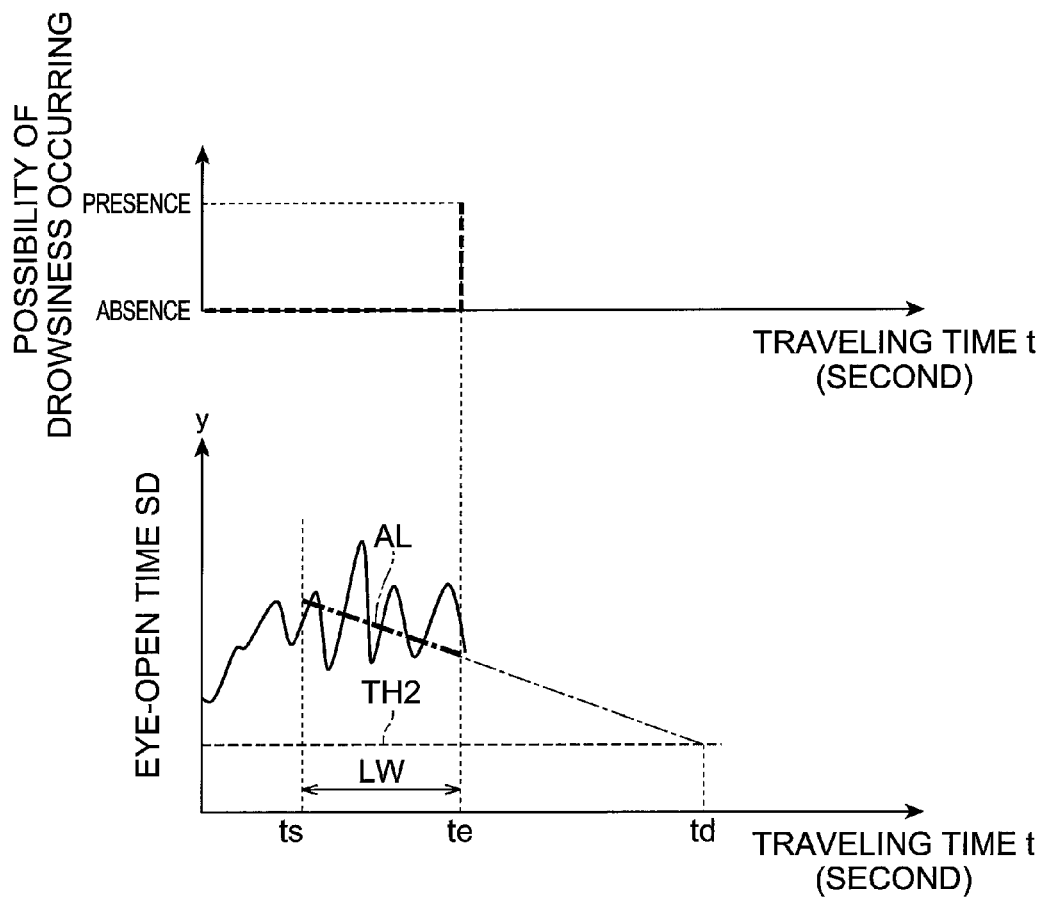
FIG. 19 is a diagram illustrating the content of the process of a drowsiness occurrence time estimating section.

Next, the drowsiness occurrence time estimating section 33 estimates the time until the driver will reach a drowsy condition on the basis of the approximate straight line AL (Step S320). As shown in FIG. 19, the drowsiness occurrence time estimating section 33 extends the approximate straight line AL and derives the time td when the driver is estimated to be in a drowsy condition. Specifically, the drowsiness occurrence time estimating section 33 extends the approximate straight line AL at the time when it is determined that there is a possibility of drowsiness occurring. This process is performed at the end time te. The drowsiness occurrence time estimating section 33 calculates the time td when the extended approximate straight line AL intersects the drowsiness occurrence threshold value TH2. The drowsiness occurrence threshold value TH2 may be set to any value. The drowsiness occurrence time estimating section 33 calculates the difference between the end time te (that is, the current time) and the time td. The drowsiness occurrence time estimating section 33 sets the difference between the end time td and the end time te as the time until the driver will reach a drowsy condition.

Then, the ECU 2 outputs a control signal to the result output section 4 or the drive assist section 6 to perform a drive assist process (Step S330). Specifically, the result output section 4 can output a voice or displays an image to notify the driver of information indicating that attentiveness has been reduced and the time until the driver will reach a drowsy condition and prompt the driver to take a rest. Alternatively, the ECU 2 can control the drive assist section 6, similarly to Step S130 in the first embodiment. When the drive assist process ends, the control process shown in FIG. 16 ends. The process starts again from Step S100.

As described above, in the physiological condition estimation device 310 according to this embodiment, the attentiveness-reduced condition determining section 31 can determine that the attentiveness of the driver is reduced on the basis of an increase in the variation in the eye-open time. Therefore, the physiological condition estimation device 310 according to this embodiment can estimate the physiological condition in an early stage before the arousal level of the driver is affected.

In the physiological condition estimation device 310 according to this embodiment, after the attentiveness-reduced condition determining section 31 determines a reduction in attentiveness, the drowsiness occurrence possibility determining section 32 can determine whether there is a possibility of the driver reaching a drowsy condition. For example, even when the determination process is performed on the basis of an increase in the variation in the eye-open time, the driver is not likely to reach a drowsy condition. For example, when it is determined that attentiveness is reduced and the drive assist process is performed without any exception, the target person is likely to become confused. Therefore, the physiological condition estimation device 310 including the drowsiness occurrence possibility determining section 32 can prevent the drive assist process from being unnecessarily performed.

In the physiological condition estimation device 310 according to this embodiment, after the attentiveness-reduced condition determining section 31 determines a reduction in attentiveness, the drowsiness occurrence time estimating section 33 can estimate the time until the target person will reach a drowsy condition on the basis of the amount of change of the variation in the eye-open time with respect to time. In this way, the physiological condition estimation device 310 according to this embodiment can perform an appropriate drive assist process on the basis of, for example, the estimated time.

Figure 20:
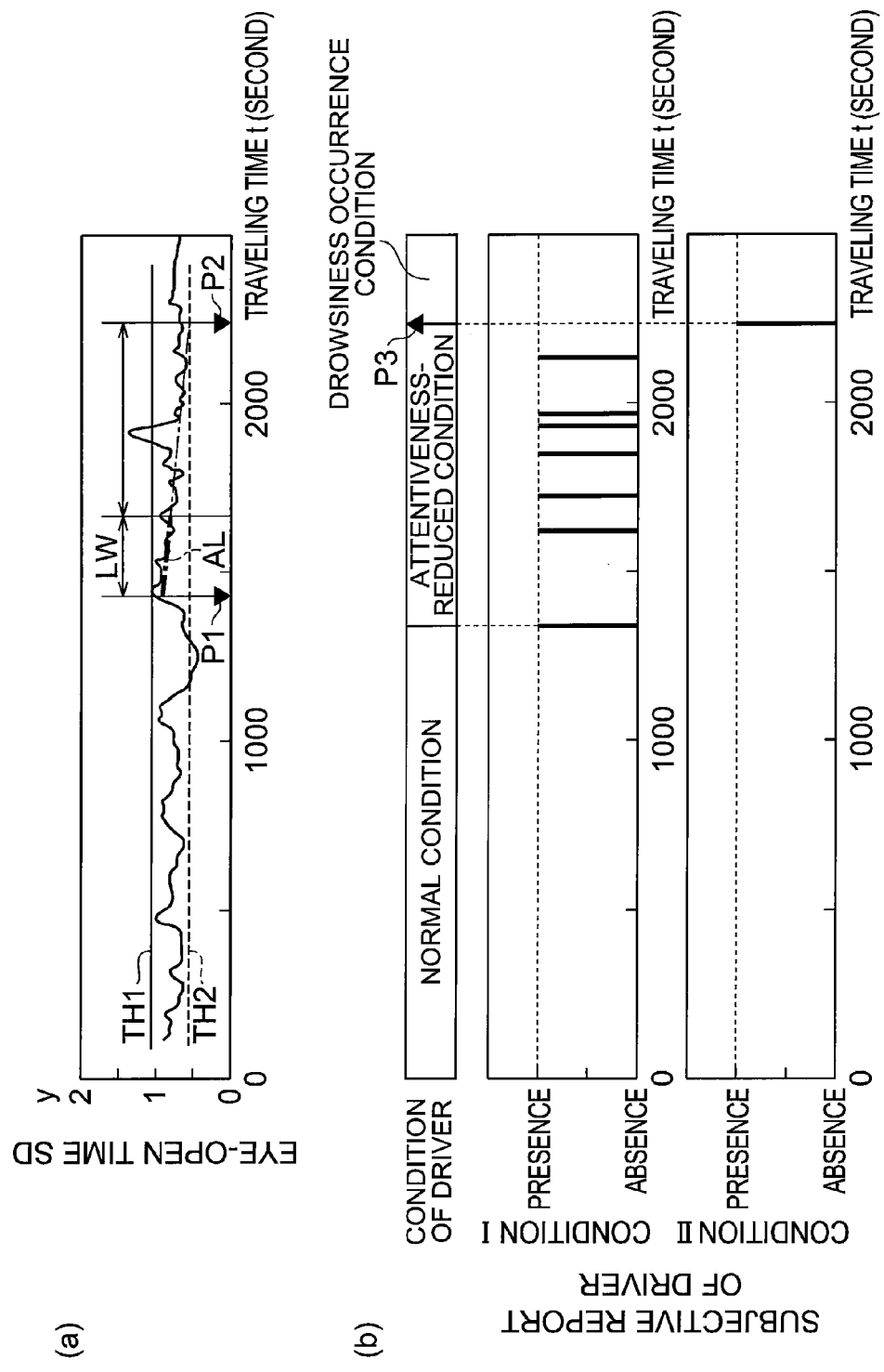
FIG. 20 is a diagram illustrating an example of the physiological condition estimation device according to the fourth embodiment.
Figure 21:
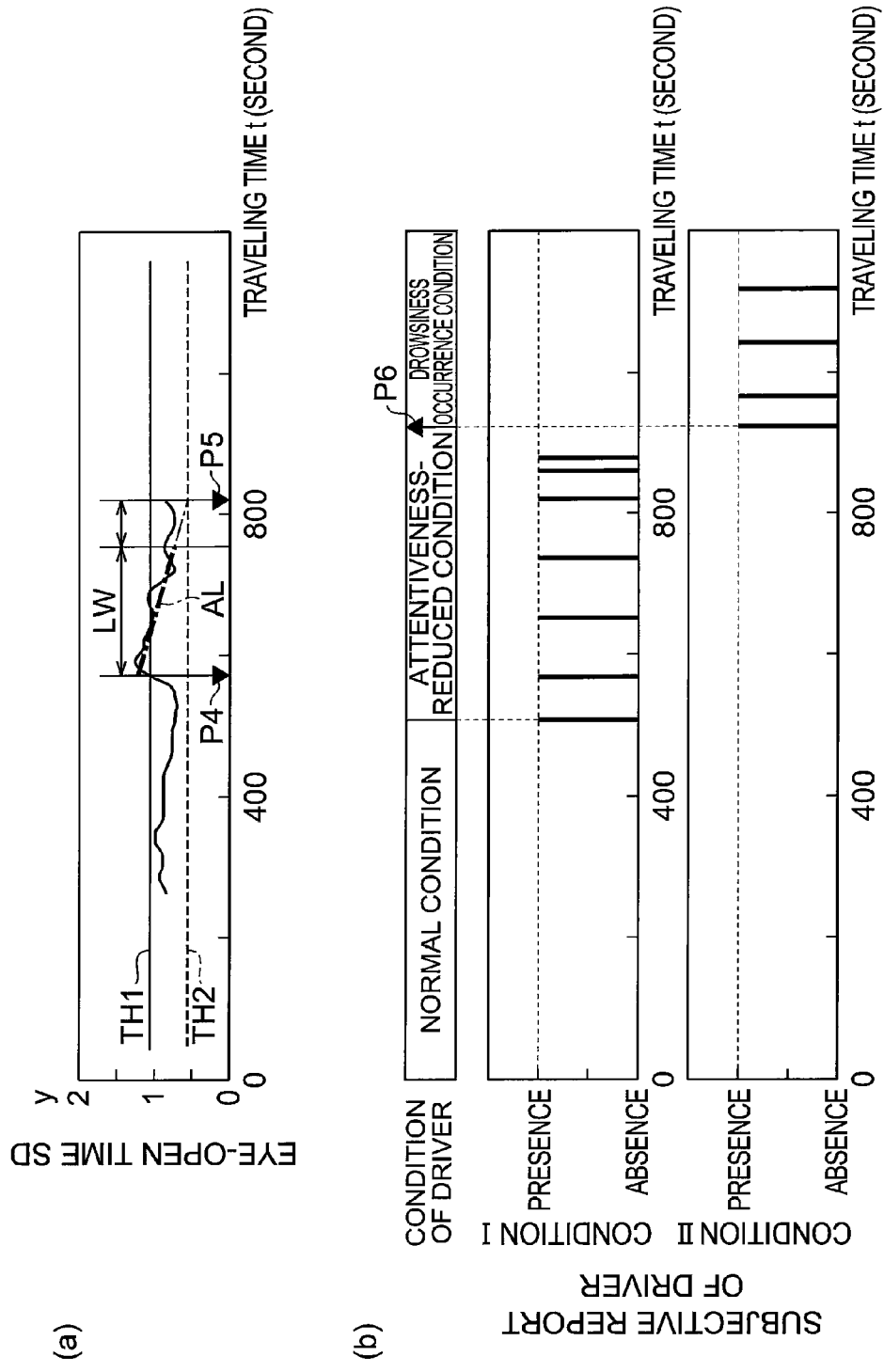
FIG. 21 is a diagram illustrating an example of the physiological condition estimation device according to the fourth embodiment.

Next, an example of the physiological condition estimation device 310 according to this embodiment will be described with reference to FIGS. 20 and 21. FIGS. 20 and 21 are diagrams illustrating the comparison between the estimation result of the physiological condition estimation device 310 according to this embodiment and a driving condition based on the subjective report of the driver. FIG. 20 shows a case in which the attentiveness-reduced condition is long and it takes a long time to change to a drowsy condition. FIG. 21 shows a case in which the attentiveness-reduced condition is short and the condition is rapidly changed to the drowsy condition.

FIG. 20(*a*) and FIG. 21(*a*) are diagrams illustrating the process result of Steps S300 to S320 shown in FIG. 16. In FIG. 20(*a*) and FIG. 21(*a*), P1 and P4 indicate the time when the variation in the eye-open time is more than the attentiveness reduction threshold value TH1, AL indicates the approximate straight line in Step S310, and P2 and P5 indicate the time when the extension line of the approximate straight line AL intersects the drowsiness occurrence threshold value TH2. That is, the physiological condition estimation device 310 presumes that the driver is in a drowsy condition at the times P2 and P5. In the example shown in FIG. 20(*a*) and FIG. 21(*a*), the coefficient N in Expression 5 is set to 3 and the width LW of the application section is set to 3 minutes. In addition, the least-squares method is used as the approximate straight line. In FIG. 20(*a*) and FIG. 21(*a*), the vertical axis indicates a normalized value. In FIG. 20(*b*) and FIG. 21(*b*), the diagram represented by "condition I" indicates the time when the driver makes a report indicating that "the driver considers that he or she is not drowsy, but wants to be stimulated for any reason". In FIG. 20(*b*) and FIG. 21(*b*), the diagram represented by "condition II" indicates the time when the driver makes a report indicating that "the driver considers that he or she wants to be stimulated since he or she is drowsy". In FIG. 20(*b*) and FIG. 21(*b*), the diagram represented by the "condition of the driver" indicates the condition of the driver acquired on the basis of the content of the report of the driver. In the diagram "condition of the driver", a region in which there is no report in both the "condition I" and the "condition II" is represented by a "normal condition", a region in which there is a report in the "condition I" is represented by an "attentiveness-reduced condition", and a region in which there is a report in the "condition II" is represented by a "drowsiness occurrence condition". P3 indicates the time when there is the first report in the "condition II". That is, drowsiness occurs in the driver at the time P3.

As shown in FIG. 20(*b*), the condition of the driver changes from the normal condition to the attentiveness-reduced condition in the vicinity of t=1350 seconds and changes from the attentiveness-reduced condition to the drowsiness occurrence condition in the vicinity of t=2230 seconds (P3). As shown in FIG. 20(*a*), the physiological condition estimation device 310 detects that the driver changes from the normal condition to the attentiveness-reduced condition in the vicinity of t=1400 seconds (P1) and presumes that the driver changes from the attentiveness-reduced condition to the drowsiness occurrence condition in the vicinity of t=2210 seconds (P2). As described above, the physiological condition estimation device 310 can detect a reduction in attentiveness with high accuracy and estimate the time required for a change in the drowsiness occurrence condition with high accuracy.

As shown in FIG. 21(*b*), the driver changes from the normal condition to the attentiveness-reduced condition in the vicinity of t=500 seconds and changes from the attentiveness-reduced condition to the drowsiness occurrence condition in the vicinity of t=920 seconds (P6). As shown in FIG. 21(*a*), the physiological condition estimation device 310 detects that the driver changes from the normal condition to the attentiveness-reduced condition in the vicinity of t=570 seconds (P4) and presumes that the driver changes from the attentiveness-reduced condition to the drowsiness occurrence condition in the vicinity of t=830 seconds (P5). In FIG. 21, the condition of the driver changes more rapidly than that in FIG. 20. Therefore, an error in the result of the example shown in FIG. 21 is more than that in the result of the example shown in FIG. 20. However, the physiological condition estimation device 310 can detect a reduction in attentiveness with sufficiently high accuracy to perform an appropriate drive assist process and estimate the time until the condition changes to the drowsiness occurrence condition with high accuracy, even though the condition of the driver is rapidly changed.

Fifth Embodiment

Next, a physiological condition estimation device 410 and a vehicle control device 400 according to a fifth embodiment of the invention will be described with reference to FIG. 22. The physiological condition estimation device 410 and the vehicle control device 400 according to the fifth embodiment are mainly different from the physiological condition estimation device 310 and the vehicle control device 300 according to the fourth embodiment in that the attentiveness reduction threshold value TH1 varies depending on an individual driver.

Figure 22:
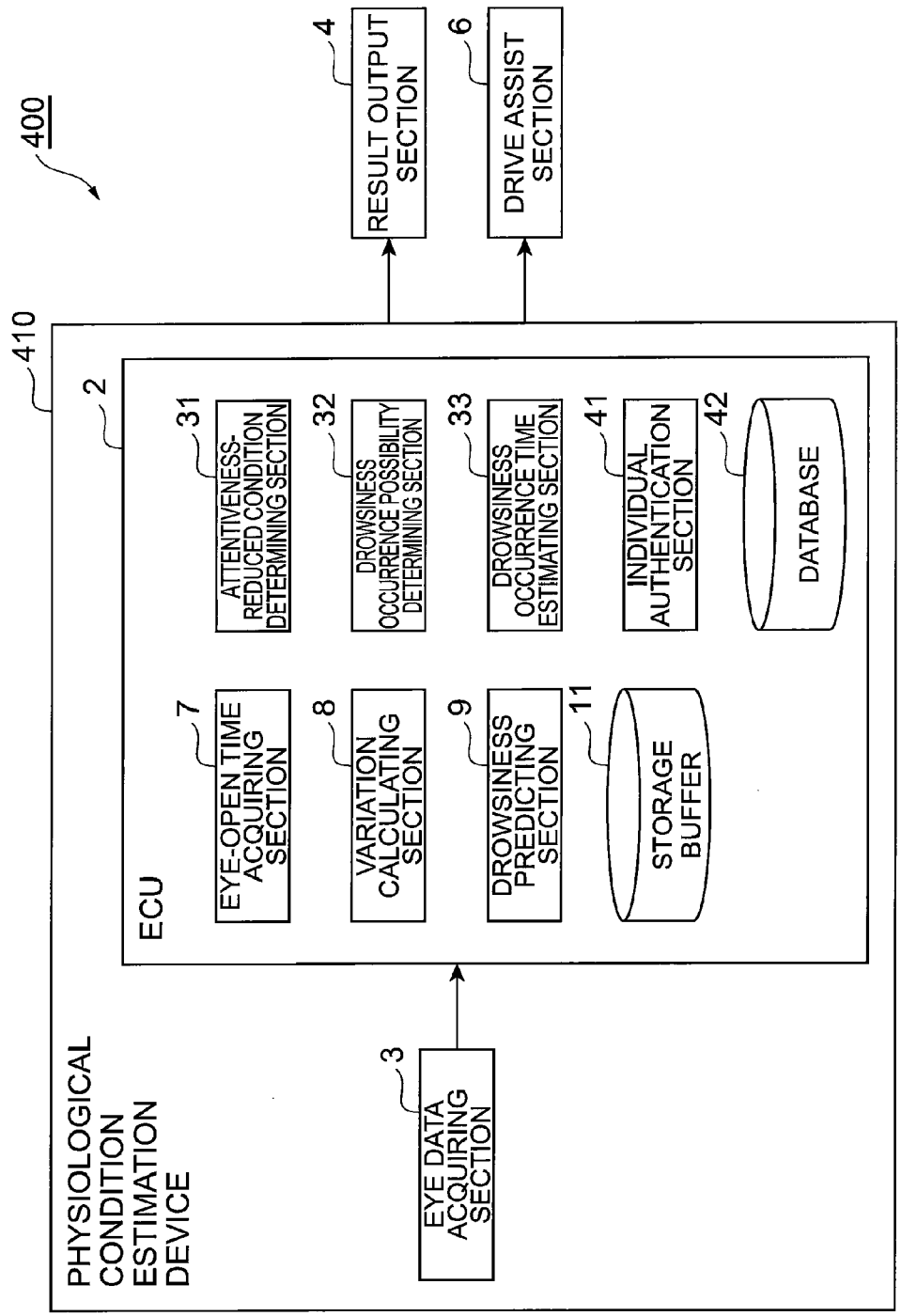
FIG. 22 a diagram illustrating the block structure of a physiological condition estimation device and a vehicle control device according to a fifth embodiment.

FIG. 22 is a diagram illustrating the block structure of the physiological condition estimation device 410 and the vehicle control device 400 according to the fifth embodiment. As shown in FIG. 22, an ECU 2 of the physiological condition estimation device 410 includes an individual authentication section 41 and a database 42. The other structures are the same as those of the physiological condition estimation device 310 and the vehicle control device 300 according to the fourth embodiment.

The individual authentication section 41 has a function of authenticating an individual driver. The database 42 has a function of storing the names of the driver and the attentiveness reduction threshold values TH1 as a database so as to be associated with each other. In addition, the database 42 has a function of outputting the attentiveness reduction threshold value TH1 according to the authentication result of the individual authentication section 41. The database 42 may store the data of the attentiveness reduction threshold value TH1 when each driver uses the physiological condition estimation device 410 at the beginning.

The physiological condition estimation device 410 having the above-mentioned structure authenticates an individual driver using the individual authentication section 41 and acquires the corresponding attentiveness reduction threshold value TH1 from the database 42. In addition, the physiological condition estimation device 410 uses the attentiveness reduction threshold value TH1 in Step S300. In this way, the physiological condition estimation device 410 according to this embodiment can perform an appropriate determination process according to the individual driver.

Sixth Embodiment

Next, a physiological condition estimation device 510 and a vehicle control device 500 according to a sixth embodiment of the invention will be described with reference to FIG. 23. The physiological condition estimation device 510 and the vehicle control device 500 according to the sixth embodiment are mainly different from the physiological condition estimation device 310 and the vehicle control device 300 according to the fourth embodiment in that the attentiveness reduction threshold value TH1 varies depending on whether the driver wears glasses.

Figure 23:
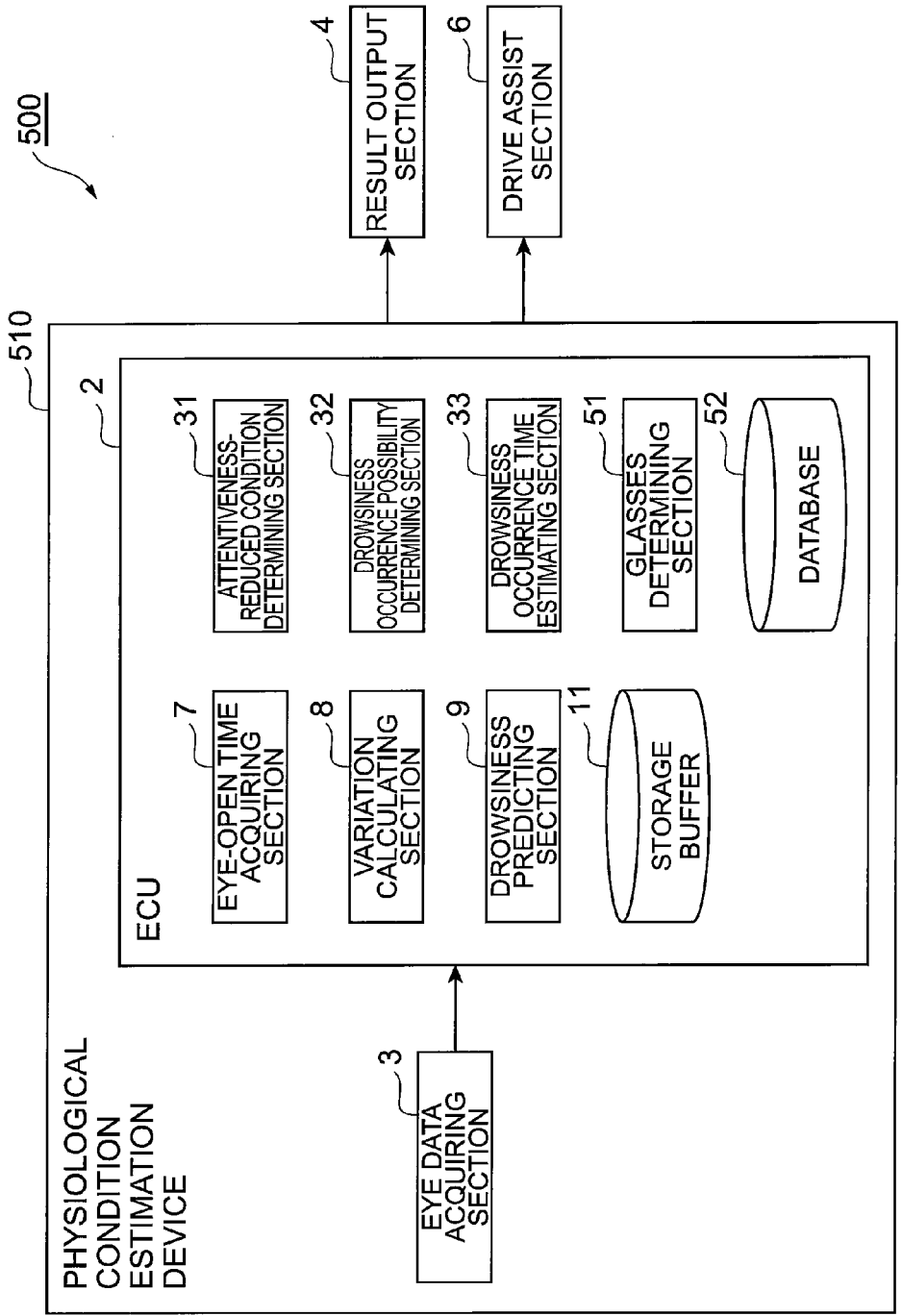
FIG. 23 is a diagram illustrating the block structure of a physiological condition estimation device and a vehicle control device according to a sixth embodiment.

FIG. 23 is a diagram illustrating the block structure of the physiological condition estimation device 510 and the vehicle control device 500 according to the sixth embodiment. As shown in FIG. 23, an ECU 2 of the physiological condition estimation device 510 includes a glasses determining section 51 and a database 52. The other structures are the same as those of the physiological condition estimation device 310 and the vehicle control device 300 according to the fourth embodiment.

The glasses determining section 51 has a function of determining whether the driver wears glasses. The glasses determining section 51 determines the existence of the glasses on the basis of data from the eye data acquiring section 3. The database 52 has a function of storing a coefficient for calculating the attentiveness reduction threshold values TH1 when there are glasses and when there are no glasses as a database.

In addition, the database 52 has a function of outputting the coefficient according to the determination result of the glasses determining section 51.

Figure 24:
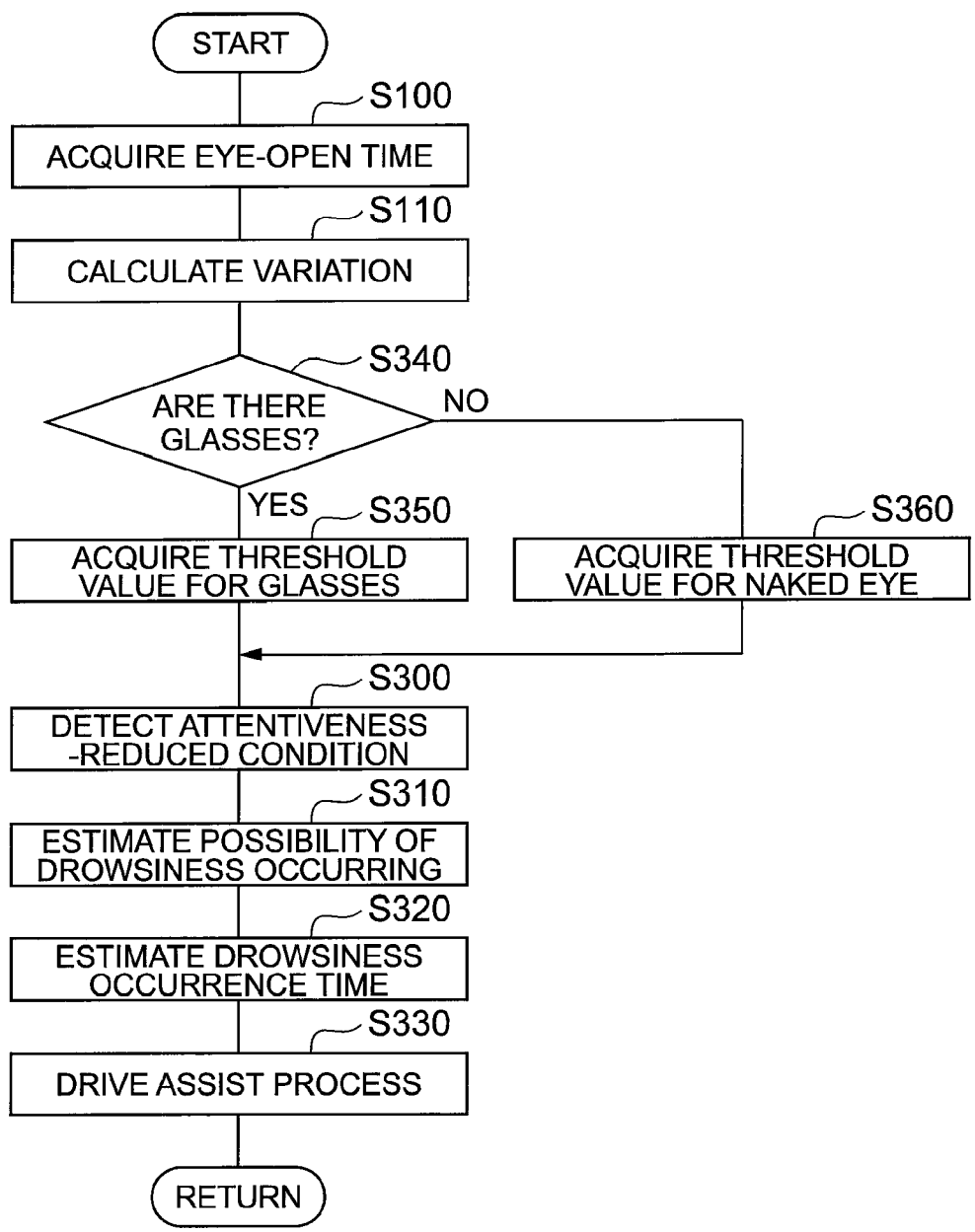
FIG. 24 is a flowchart illustrating an information processing operation of the physiological condition estimation device according to the sixth embodiment.

Next, the operation of the physiological condition estimation device 510 and the vehicle control device 500 according to this embodiment will be described with reference to FIG. 24. FIG. 24 is a flowchart illustrating an information processing operation of the physiological condition estimation device 510 according to this embodiment. The information processing operation shown in FIG. 24 is repeatedly performed by the ECU 2 of the physiological condition estimation device 510 while the vehicle is traveling from the start of driving.

As shown in FIG. 24, the eye-open time acquiring section 7 acquires the eye-open time of the driver and stores the acquired eye-open time data in the storage buffer 11 (Step S100). Then, the variation calculating section 8 calculates a variation in the eye-open time, that is, the standard deviation of the eye-open time on the basis of the eye-open time data (Step S110). In Steps S100 and S110, the same process as that in Steps S100 and S110 of FIG. 2 is performed.

The glasses determining section 51 determines whether the driver wears glasses (Step S340). In Step S340, when the glasses determining section 51 determines that the driver wears glasses, the attentiveness-reduced condition determining section 31 acquires the attentiveness reduction threshold value TH1 for glasses on the basis of the data from the database 52 (Step S350). Specifically, the attentiveness-reduced condition determining section 31 downloads a coefficient N for glasses from the database 52 and performs the calculation of Expression 5 on the basis of the coefficient. The coefficient N for glasses may be set to, for example, 5. In Step S340, when the glasses determining section 51 determines that the driver does not wear glasses, the attentiveness-reduced condition determining section 31 acquires the attentiveness reduction threshold value TH1 for the naked eye on the basis of the data from the database 52 (Step S360). Specifically, the attentiveness-reduced condition determining section 31 downloads the coefficient N for the naked eye from the database 52 and performs the calculation of Expression 5 on the basis of the coefficient. The coefficient N for the naked eye may be set to, for example, 3. Then, Steps S300 to S330 are performed, similarly to FIG. 16.

When the driver wears glasses, eyestrain occurs in the driver even though the attentiveness of the driver is not reduced and a variation in the eye-open time is more than that when the driver does not wear glasses. The physiological condition estimation device 510 according to this embodiment changes the attentiveness reduction threshold value TH1 depending on whether the driver wears glasses. In this way, it is possible to perform appropriate determination.

Seventh Embodiment

Next, a physiological condition estimation device 610 and a vehicle control device 600 according to a seventh embodiment of the invention will be described with reference to FIG. 25. The physiological condition estimation device 610 and the vehicle control device 600 according to the seventh embodiment are mainly different from the physiological condition estimation device 10 and the vehicle control device 1 according to the first embodiment in that the physiological condition of the driver is estimated on the basis of the amount of change of a variation in the eye-open time with respect to time.

Figure 25:
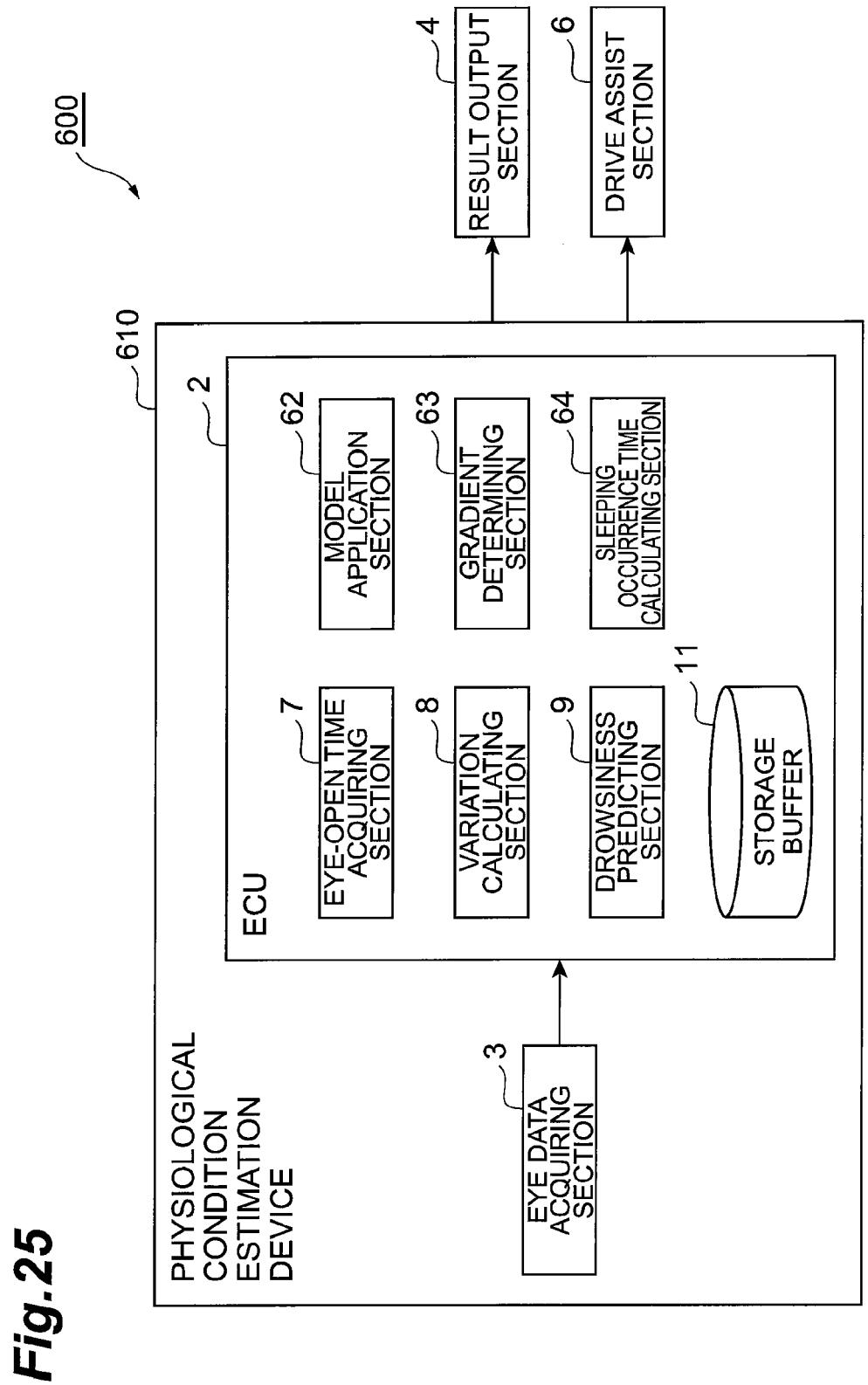
FIG. 25 is a diagram illustrating the block structure of a physiological condition estimation device and a vehicle control device according to a seventh embodiment.

FIG. 25 is a diagram illustrating the block structure of the physiological condition estimation device 610 and the vehicle control device 600 according to the seventh embodiment. As shown in FIG. 25, an ECU 2 of the physiological condition estimation device 610 includes a model application section 62, a gradient determining section (physiological condition change determining unit) 63, and a sleeping occurrence time calculating section (physiological condition estimating unit) 64. The other structures are the same as those of the physiological condition estimation device 10 and the vehicle control device 1 according to the first embodiment.

The model application section 62 has a function of applying an approximate line to a variation in the eye-open time. The kind of approximate expression to be applied is not particularly limited. Any approximate expression may be used as long as it can approximate eye-open time variation data with high accuracy. For example, a straight line whose gradient and intercept are determined may be used. In addition, a method of evaluating the validity of the gradient or intercept is not particularly limited, but any method may be used as long as it can evaluate the validity. For example, a least-squares method may be used. The gradient of the approximate line corresponds to the amount of change in a variation in the eye-open time with respect to time in the claims.

The gradient determining section 63 has a function of determining the magnitude of the gradient of the approximate line obtained by the model application section 62 (that is, the amount of change of the variation in the eye-open time with respect to time). Specifically, the gradient determining section 63 may compare the magnitude of the gradient of the approximate line with a predetermined set value to perform the determination process. In addition, the gradient determining section 63 has a function of determining a change in the physiological condition on the basis of the gradient of the approximate line. Specifically, when the gradient is reduced, the gradient determining section 63 may determine that it is the condition in which the arousal level is reducing. When the gradient increases, the gradient determining section 63 may determine that it is the condition in which the arousal level is increasing.

The sleeping occurrence time calculating section 64 has a function of estimating the future physiological condition, that is, a function of predicting the physiological condition, on the basis of the gradient of the approximate line. Since calculation is performed on the basis of the gradient of the approximate line, it is possible to presume a reduction in the arousal level to a value that will cause an adverse effect on a driving operation in the future (sleeping occurrence condition). The sleeping occurrence time calculating section 64 also has a function of calculating the time when sleeping occurs. The sleeping occurrence time calculating section 64 has a function of "estimating" a future condition of reduction in the arousal level to a value that will cause an adverse effect on the driving, driving operation. Therefore, the function of the sleeping occurrence time calculating section 64 is different from the function of the drowsiness predicting section 9 that can "determine" a slight reduction in the current arousal level which makes possibility of causing an adverse effect on the driving operation in the future.

Figure 26:
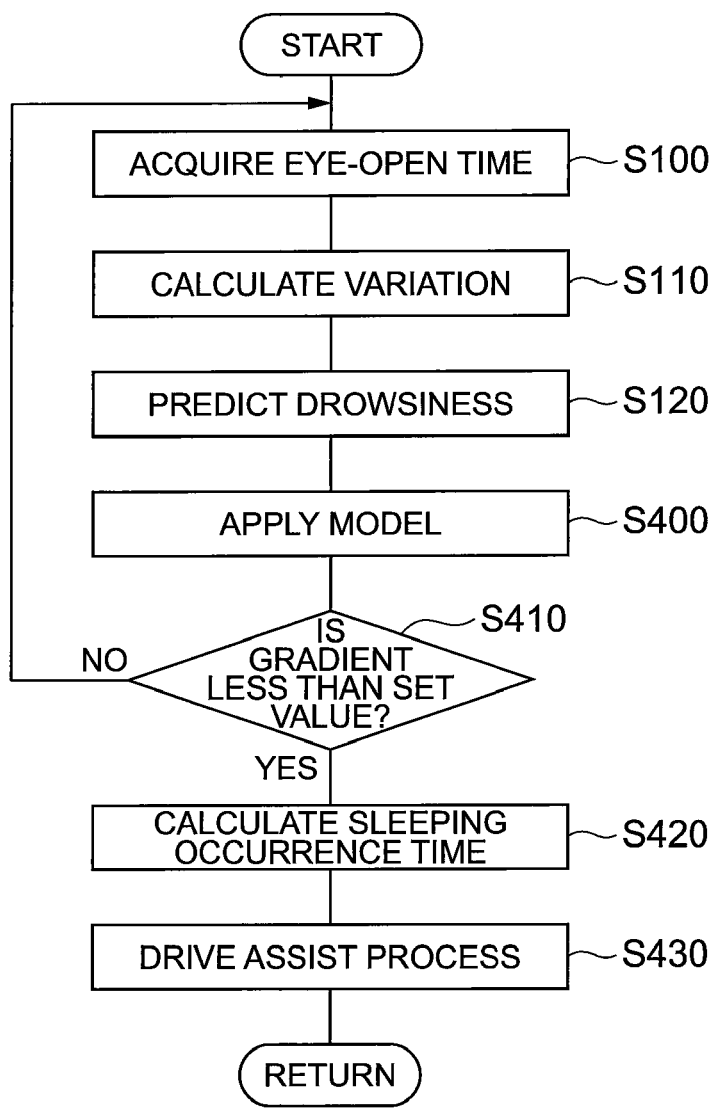
FIG. 26 is a flowchart illustrating an information processing operation of the physiological condition estimation device according to the seventh embodiment.

Next, the operation of the physiological condition estimation device 610 and the vehicle control device 600 according to this embodiment will be described with reference to FIG. 26. FIG. 26 is a flowchart illustrating an information processing operation of the physiological condition estimation device 610 according to this embodiment. The information processing operation shown in FIG. 26 is repeatedly performed by the ECU 2 of the physiological condition estimation device 610 while the vehicle is traveling from the start of driving.

As shown in FIG. 26, the eye-open time acquiring section 7 acquires the eye-open time of the driver and stores the acquired eye-open time data in the storage buffer 11 (Step S100). Then, the variation calculating section 8 calculates a variation in the eye-open time, that is, the standard deviation of the eye-open time on the basis of the eye-open time data (Step S110). Then, the drowsiness predicting section 9 predicts drowsiness (Step S120). In Steps S100, S110, and S120, the same process as that in Steps S100, S110, and S120 of FIG. 2 is performed.

When the drowsiness predicting section 9 determines that it is the condition in which the arousal level of the driver is low (that is, when drowsiness is predicted), the model application section 62 allies an approximate line to the variation in the eye-open time (Step S400). The content of the model application process will be described in detail below with reference to FIG. 27. FIG. 27 is a diagram illustrating the content of the model application process. FIG. 27(*a*) is a diagram illustrating whether there is a drowsiness prediction output in Step S120. In FIG. 27(*a*), it is assumed that there is a drowsiness prediction output at the rising time of the detection position where the duration time for which the average value of the eye-open time SD is less than the amplitude threshold value Th_a is more than the time threshold value Th_t in FIG. 6(*b*) and the time is referred to as a time t0. In FIG. 27(*b*), an approximate line of the diagram of the eye-open time SD is written in the graph of the eye-open time SD corresponding to FIG. 5(*a*). As shown in FIG. 27(*b*), the model application section 62 calculates an approximate line for the eye-open time SD of the section (the section from a time t0-tp to the time t0) from the time t0 to the past tp seconds. The kind of approximate expression is not particularly limited, but any approximate expression may be used as long as it can approximate the eye-open time variation data with high accuracy. In this embodiment, a case in which a straight line is applied will be described. The approximate line is represented by Expression 7 and is obtained by determining coefficients A and B. A method of evaluating the validity of the coefficient A and the coefficient B is not particularly limited, but any method may be used as long as it can evaluate the validity. For example, a least-squares method may be used. The gradient of the approximate line corresponds to the amount of change in a variation in the eye-open time with respect to time in the claims.

$$y = At + B \qquad \text{[Expression 7]}$$

After the approximate line is calculated in Step S400, the gradient determining section 63 determines the magnitude of the gradient of the approximate line that is given as the coefficient A (Step S410). The gradient determining section 63 compares the magnitude of the gradient A of the approximate line with a predetermined set value Gt to perform the determination process. When the relationship A<Gt is established, the gradient determining section 63 determines that the gradient is less than the set value and it is the condition in which the arousal level is reducing. When the relationship A≤Gt is established, the gradient determining section 63 determines that the gradient is equal to or more than the set value and it is the condition in which the arousal level is not reducing, or the arousal level is increasing. When it is determined in Step S410 that the gradient is equal to or more than the set value, the process returns to S100. Then, the process is repeated again from Step S100.

When it is determined in Step S410 that the gradient is less than the set value, the sleeping occurrence time calculating section 64 calculates the time until the arousal level is reduced to a value that causes an adverse effect on the driving operation on the basis of the approximate line calculated in Step S400 (Step S420). As shown in FIG. 27(b), the sleeping occurrence time calculating section 64 extends the approximate line calculated in Step S400 to future time and estimates the time tth when the extension line is identical to a predetermined threshold value yth as the time when sleeping occurs. Specifically, the sleeping occurrence time calculating section 64 substitutes the coefficient A and the coefficient B of the approximate line into Expression 8 to calculate the sleeping occurrence time tth. In addition, the sleeping occurrence time calculating section 64 substitutes the sleeping occurrence time tth into Expression 9 to calculate the remaining time ts before the occurrence of sleeping which indicates the "time remaining until sleeping occurs".

$$tth = \left| \frac{yth - B}{A} \right| \quad \text{[Expression 8]}$$

$$ts = tth - t0 \quad \text{[Expression 9]}$$

The ECU 2 outputs a control signal to the result output section 4 or the drive assist section 6 to perform a drive assist process (Step S430). Specifically, the result output section 4 may output a voice or display an image to inform the driver that sleeping will occur ts seconds later and prompt the driver to take a rest. In addition, the drive assist section 6 is controlled to perform the following operation: an operation of increasing boost pressure such that the vehicle can be stopped immediately after the brake pedal is pressed; an operation of evacuating the vehicle to a safe position and forcibly operating the brake such that the driver takes a rest with reference to map information of a navigation apparatus; an operation of rolling up a seatbelt so as to facilitate the operation of an occupant protection device, such as the operation of an occupant protection bag or the movement of a headrest for reducing a whiplash injury; an operation of detecting the lane with a camera and applying steering force such that lane departure does not occur or the vehicle keeps its lane; an operation of detecting the distance from the vehicle in front with a millimeter-wave radar or a laser beam and maintaining a predetermined inter-vehicle distance, or setting the inter-vehicle distance to a large value; an operation of monitoring a surrounding obstacle with a camera image and assisting an avoiding operation using the brake or the steering wheel; or an operation of reducing the number of revolutions of the engine. When the drive assist process ends, the control process shown in FIG. 26 ends. Then, the process starts again from Step S100.

In the method of detecting the physiological condition according to the related art, it is possible to detect a reduction in the arousal level to a value that affects the operation of the vehicle, but it is difficult to detect a slight reduction in the arousal level before the stage in which the reduction in the arousal level to a value that affects the operation of the vehicle and thus prevent an error in the driving of the vehicle. However, according to the physiological condition estimation device 610 of this embodiment, the eye-open time of the driver is acquired and the physiological condition of the driver is estimated on the basis of the amount of change of the variation in the eye-open time with respect to time (that is, for example, the gradient of the modeled graph, such as the approximate line). Therefore, it is possible to estimate preliminarily a significant reduction in the arousal level to a value at which an error in the driving of the vehicle will occur in the future even in the stage in which the arousal level is slightly reduced. In particular, the vehicle control device 600 according to this embodiment controls the vehicle on the basis of the amount of change of the variation in the eye-open time of the driver with respect to time to support driving before the stage in which an error occurs in the driving of the vehicle. In this way, it is possible to improve the safety of the operation of an apparatus, such as a vehicle.

Figure 28:
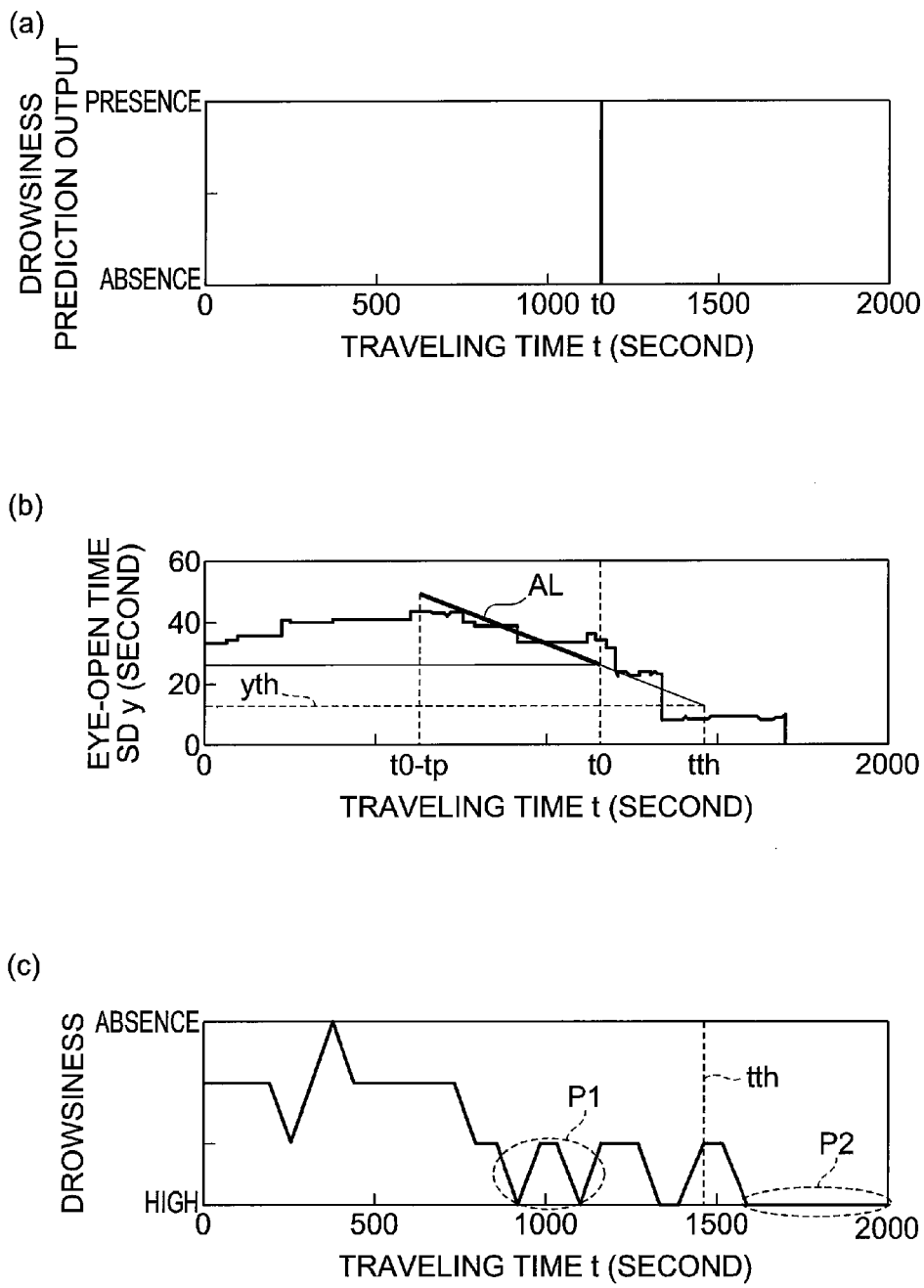
FIG. 28 is a view illustrating the relationship between the drowsiness level of the examinee and each diagram illustrating the content of the process of the physiological condition estimation device when the physiological condition of the driver, who is the examinee, is estimated.

Next, an example of the physiological condition estimation device 610 according to this embodiment will be described with reference to FIG. 28 and FIG. 29. FIG. 28 shows the relationship between diagrams illustrating the content of the process of the physiological condition estimation device 610 when the physiological condition of the driver, who is an examinee, is estimated and the drowsiness level of the examinee. FIG. 28(a) is a diagram illustrating whether there is a drowsiness prediction output in Step S120. FIG. 28(b) is a diagram illustrating the estimation of the sleeping occurrence time from the approximate line of the standard deviation of the eye-open time. FIG. 28(c) is a diagram illustrating the level of drowsiness reported by the examinee. FIG. 29 is a diagram illustrating the value of each constant and each unit in the example shown in FIG. 28. In this example, as shown in FIG. 28(a), the drowsiness prediction output is detected at a time t0=1120 seconds. Since tp is 500 seconds, the approximate line AL of the standard deviation of the eye-open time in the section from a time t0-tp to the time t0, that is, the section in the vicinity of 620 seconds to 1120 seconds. The approximate line AL is calculated as follows: y=−0.052t+86.2.

As such, since the gradient of the approximate line AL is −0.052, the gradient A is less than Gt (=0), it is determined that the gradient is less than the set value. In this way, yth=10, A=−0.052, and B=86.2 are substituted into Expression 8 and the sleeping occurrence time tth=1427 seconds is calculated. In addition, the time ts=307 seconds remaining before the occurrence of sleeping is calculated. When the relationship between this result and the drowsiness level of the examinee is verified, as shown in FIG. 28(c), the driver loses consciousness several tens of seconds after the estimated time tth (a region P2 in FIG. 28(c)). As such, according to the physiological condition estimation device 610 of the invention, it is possible to accurately presume the time remaining until the occurrence of sleeping with an error tolerance of about one minute. As can be seen from FIG. 28(c), the arousal level is slightly reduced in the vicinity of the time t0 when there is a drowsiness prediction output (a region P1 in FIG. 28(c)). When the threshold value yth is set to a large value, it is possible to estimate the time when the arousal level will be reduced earlier.

Eighth Embodiment

Next, a physiological condition estimation device 710 and a vehicle control device 700 according to an eighth embodiment of the invention will be described with reference to FIGS. 30 to 32. The physiological condition estimation device 710 and the vehicle control device 700 according to the eighth embodiment are mainly different from the physiological condition estimation device 610 and the vehicle control device 600 according to the seventh embodiment in that, when the sleeping prediction result has been output to the driver, it is possible to cancel the sleeping prediction output or update the drowsiness prediction output with new information.

Figure 30:
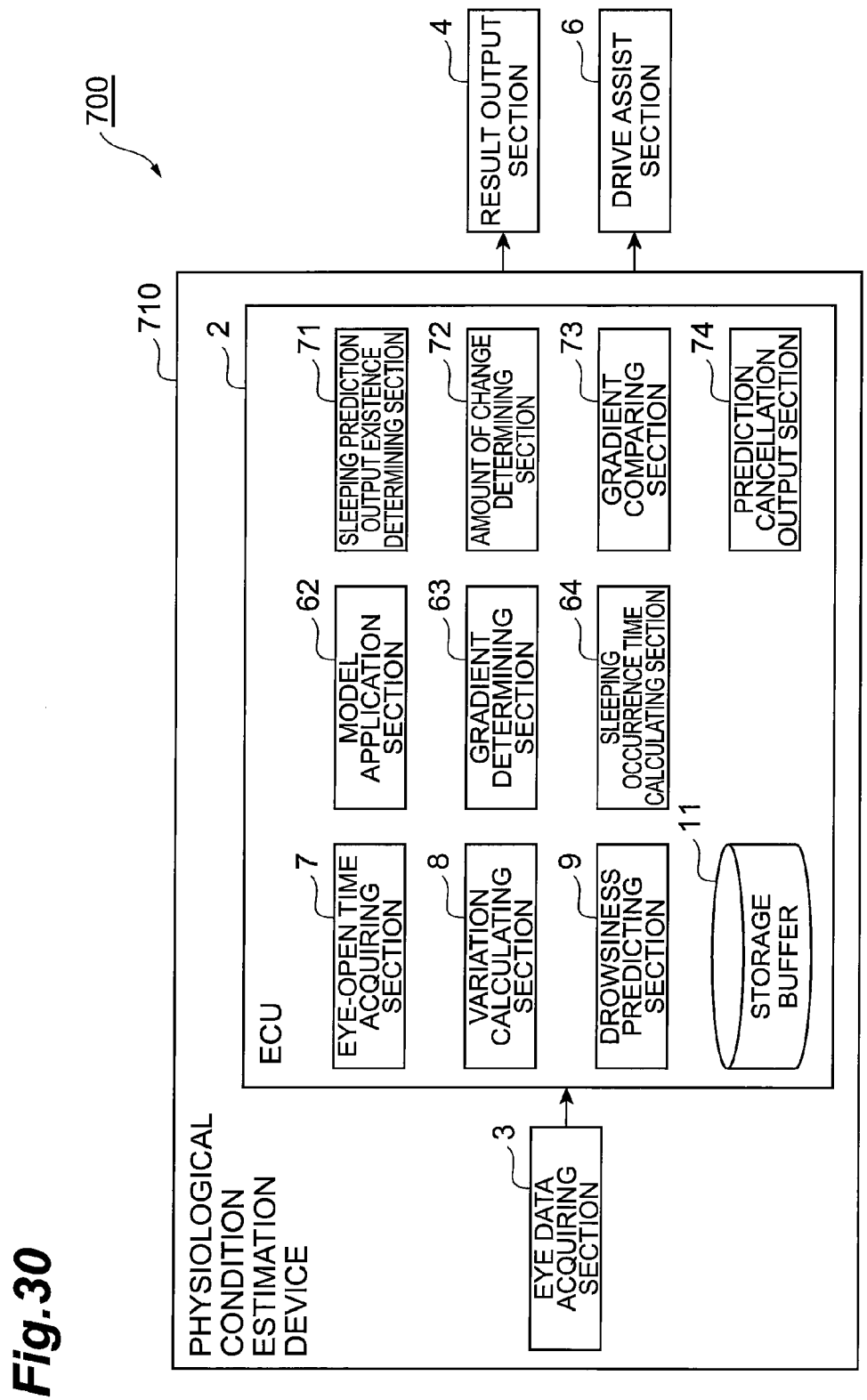
FIG. 30 is a diagram illustrating the block structure of a physiological condition estimation device and a vehicle control device according to an eighth embodiment.

FIG. 30 is a diagram illustrating the block structure of the physiological condition estimation device 710 and the vehicle control device 700 according to the eighth embodiment. As shown in FIG. 30, an ECU 2 of the physiological condition estimation device 710 further includes a sleeping prediction output existence determining section 71, a amount of change determining section 72, a gradient comparing section 73, and a prediction cancellation output section 74. Each of the components functions as an estimation result update unit in the claims. The other structures are the same as those of the physiological condition estimation device 610 and the vehicle control device 600 according to the seventh embodiment.

The sleeping prediction output existence determining section 71 has a function of determining whether the sleeping prediction result has been output to the driver. For example, when the sleeping occurrence time has been calculated and the time remaining until the occurrence of sleeping has been displayed on, for example, a display of the result output section 4, the sleeping prediction output existence determining section 71 determines that the sleeping prediction result has been output. When the remaining time has not been displayed or notified, the sleeping prediction output existence determining section 71 determines that the sleeping prediction result has not been output.

The amount of change determining section 72 has a function of calculating the amount of change of the variation in the eye-open time at the current time and determining whether the amount of change is equal to or more than a predetermined set value. Specifically, the amount of change determining section 72 calculates the gradient of the approximate line on the basis of the standard deviation of the eye-open time in the section from the current time t0 to a time t0-tp and compares the gradient with a predetermined set value to determine whether the arousal level tends to increase or decrease.

The gradient comparing section 73 has a function of comparing the amount of change of the variation in the eye-open time at the previous time with the amount of change of the variation in the eye-open time at the current time. When the amount of change at the current time is less than that at the previous time, it is determined that the gradient increases in the negative direction. This means that the variation in the eye-open time has a strong tendency to decrease. Therefore, it is determined that the time until the occurrence of sleeping is short. When the amount of change at the current time is more than that at the previous time, it is determined that the gradient increases in the positive direction. This means that the variation in the eye-open time has a strong tendency to increase. Therefore, it is determined that the time until the occurrence of sleeping is long or drowsiness does not occur.

The prediction cancellation output section 74 has a function of removing the sleeping prediction result that has been output to the driver and transmitting information indicating that sleeping prediction has been cancelled. As a method of transmitting the information, an image may be displayed on a display of the result output section 4 or a voice may be output from a speaker of the result output section 4.

Next, the operation of the physiological condition estimation device 710 and the vehicle control device 700 according to this embodiment will be described with reference to FIG. 31. FIG. 31 is a flowchart illustrating an information processing operation of the physiological condition estimation device 710 according to this embodiment. The information processing operation shown in FIG. 31 is repeatedly performed by the ECU 2 of the physiological condition estimation device 710 while the vehicle is traveling from the start of driving.

Figure 31:
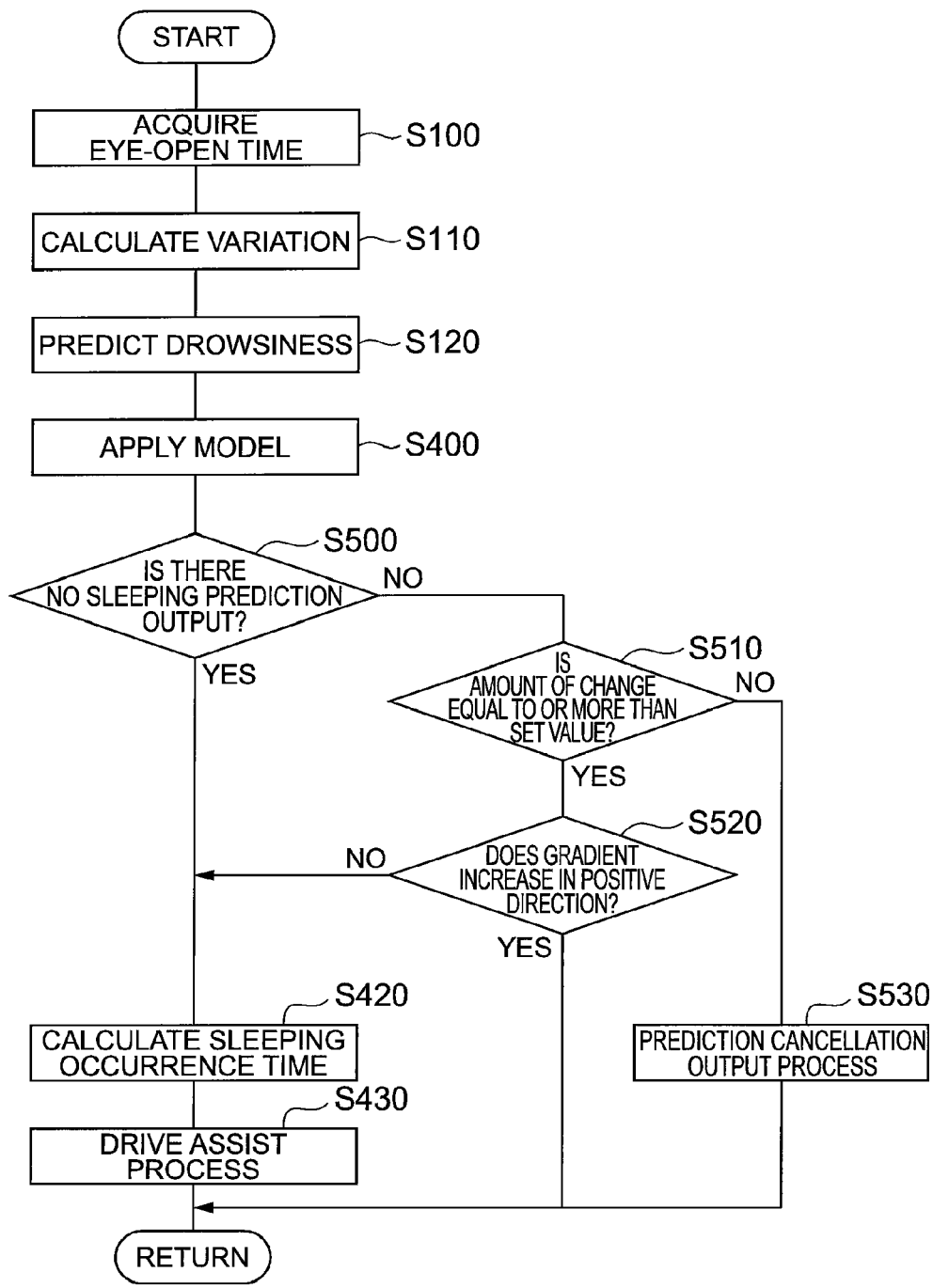
FIG. 31 is a flowchart illustrating an information processing operation of the physiological condition estimation device according to the eighth embodiment.
Figure 32:
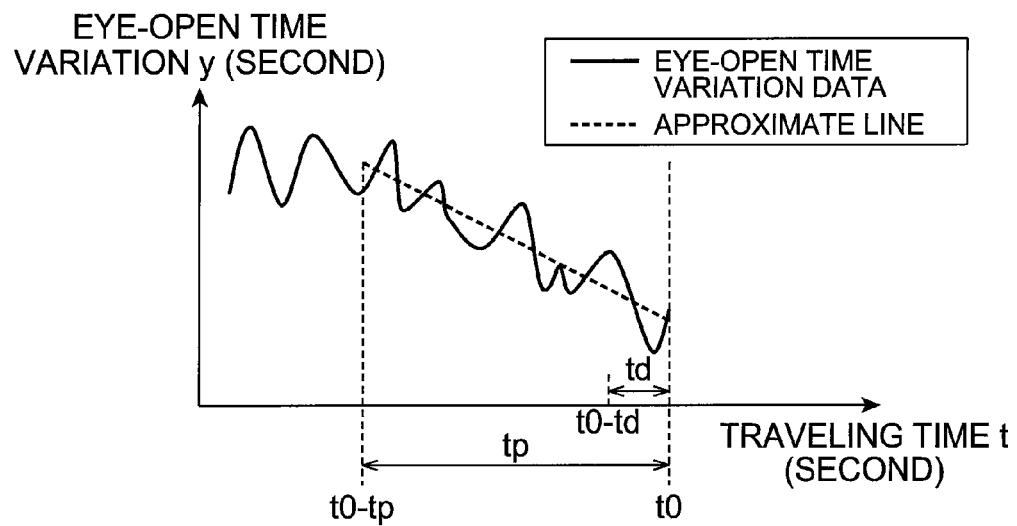
FIG. 32 is a diagram illustrating the content of a gradient comparing process.

As shown in FIG. 31, the eye-open time acquiring section 7 acquires the eye-open time of the driver and stores the acquired eye-open time data in the storage buffer 11 (Step S100). The variation calculating section 8 calculates the standard deviation of the eye-open time (Step S110). The drowsiness predicting section 9 predicts the drowsiness of the driver (Step S120). The model application section 62 applies an approximate line to the variation in the eye-open time (Step S400). In Steps S100 to S400, the same process as that in Steps S100 to S400 of FIG. 26 is performed. Then, the sleeping prediction output existence determining section 71 determines whether the sleeping prediction result has been output to the driver (Step S500). In Step S500, specifically, when the sleeping occurrence time has been calculated and the time remaining until the occurrence of sleeping has been displayed on, for example, the display of the result output section 4, the control process proceeds to a variation determination process (Step S510). On the other hand, in Step S500, when it is determined that the sleeping prediction result has not been output, the control process proceeds to a sleeping occurrence time calculating process (Step S420) and a drive assist process is performed (Step S430). In Steps S420 and S430, the same process as that in Steps S420 and S430 of FIG. 26 is performed.

In Step S510, the amount of change determining section 72 calculates the amount of change of the variation in the eye-open time at the current time and determines whether the amount of change is equal to or more than a predetermined set value. The amount of change determining section 72 calculates the gradient of the approximate line on the basis of the standard deviation of the eye-open time in the section from the current time t0 to a time t0-tp. Specifically, the approximate line is represented by the same expression as Expression 7 in the seventh embodiment and the coefficient A corresponds to the amount of change of the variation (corresponding to the amount of change in a variation in the eye-open time with respect to time in the claims). A method of evaluating the validity of the coefficient A and the coefficient B is not particularly limited, but any method may be used as long as it can evaluate the validity. For example, a least-squares method may be used. When the coefficient A indicating the gradient is obtained, the coefficient A is compared with a predetermined set value TH1. The range of TH1 is set so as to satisfy TH1>0. When the coefficient A is equal to or less than the set value TH1, that is, when the relationship A≤TH1 is established, it is determined that the arousal level tends to be reduced and the process proceeds to a gradient comparing process (Step S520). On the other hand, when the coefficient A is more than the set value TH1, that is, the relationship A>TH1 is established, it is determined that the arousal level tends to increase and the process proceeds to a prediction cancellation output process (Step S530).

In Step S520, the gradient comparing section 73 compares the amount of change of the variation in the eye-open time at the previous time with the amount of change of the variation in the eye-open time at the current time. Specifically, as shown in FIG. 32, the amount of change (referred to as A1) at the current time is obtained from the gradient of the approximate line at the time t0. The amount of change at the previous time is obtained from the gradient (referred to as A2) of the approximate line at the time t0-td. In addition, td is given by the process cycle time of the physiological condition estimation device 710. In this case, when the amount of change at the current time is less than that at the previous time, that is, when the relationship A1<A0 is established, it is determined that the gradient increases in the negative direction. When the relationship A1<A0 is established, the variation in the eye-open time has a strong tendency to decrease. Therefore, it is determined that the time remaining until the occurrence of sleeping is short and it is necessary to calculate the sleeping occurrence time again. Therefore, when it is determined in Step S520 that the gradient increases in the negative direction, the process proceeds to a sleeping occurrence time calculation process to calculate the drowsiness occurrence time again (Step S420). Then, a drive assist process is performed (Step S430) and then the process shown in FIG. 31 ends. Then, the process starts again from Step S100. In Steps S420 and S430, the same process as that in Steps S420 and S430 of FIG. 26 in the seventh embodiment is performed. On the other hand, when the amount of change at the current time is equal to or more that that at the previous time, that is, when the relationship A1≥A0 is established, it is determined that the gradient increases in the positive direction and the process shown in FIG. 31 ends. Then, the process starts again from Step S100.

In Step S530, the prediction cancellation output section 74 removes the sleeping prediction result that has been output to the driver and transmits information indicating that sleeping prediction has been cancelled to the driver. As a method of transmitting the information, the information is displayed as an image on the display of the result output section 4 or it is output as a voice from the speaker. When Step S530 ends, the process shown in FIG. 31 ends. Then, the process starts again from Step S100.

As described above, in the physiological condition estimation device 710 according to this embodiment, it is possible to update the time required for a change in the physiological condition on the basis of the gradient of the approximate line, that is, an increase or decrease in the amount of change of the approximate line with respect to time. In this way, for example, the gradient of the approximate line increases when the variation in the eye-open time increases. Therefore, it is possible to increase the estimated time until the physiological condition will change or cancel the estimated time. The gradient of the approximate line decreases when the variation in the eye-open time is reduced. Therefore, it is possible to derive a new estimated time and update the estimated time. In this way, it is possible to reflect the latest eye-opening condition of a target person in the estimation result and thus improve the accuracy of estimation.

The physiological condition estimation device and the vehicle control device according to the invention are not limited to the above-described embodiments.

For example, in the above-described embodiments, a reduction in drowsiness, that is, the arousal level is determined as the physiological condition. However, a reduction in the attentiveness (absentminded condition) of the driver or the waking condition (eye-open condition) of the driver may be determined on the basis of a variation in the eye-open time.

In the processes shown in FIGS. 2, 9, 12, 16, 24, 26, and 31, the variation calculating section 8 calculates the variation in the degree of the opening of the eye with the standard deviation. However, the variation in the degree of the opening of the eye may be calculated by other statistical processes, such as variance or a histogram.

In the above-described embodiments, the variation in the eye-open time is calculated by the statistical process. However, for example, among the eye-open times within a predetermined sampling time, the number of eye-open times that are longer than a predetermined threshold value and the number of eye-open times that are shorter than the predetermined threshold value may be counted and the variation in the eye-open time may be determined on the basis of the ratio of the count values.

In the above-described embodiments, even after the drowsiness predicting section 9 presumes a reduction in the arousal level, the variation calculating section 8 or the drowsiness predicting section 9 continuously processes information. However, after the drowsiness predicting section 9 presumes a reduction in the arousal level, the operation mode may be changed to the drowsiness detection mode, the eye-closed time of the driver or the degree of the opening of the eye of the driver may be measured by a known technique, thereby directly detecting drowsiness. In this case, the drowsiness predicting section 9 presumes that drowsiness will occur in the future and changes the operation mode to the mode in which the drowsiness of the driver at the current time is monitored in real time. In this way, it is possible to accurately monitor the condition of the driver from a waking condition to the loss of consciousness and thus a proper drive assist process.

In the above-described embodiments, the physiological condition estimation device is incorporated into the vehicle control device to estimate the physiological condition of the driver of the vehicle, but the invention is not limited thereto. The physiological condition estimation device may be provided in other carriages and may be applied to various drivers.

In the above-described embodiments, the time until the occurrence of drowsiness, that is, the time required for a change in the physiological condition is estimated on the basis of the gradient of the approximate line, that is, the amount of change of a variation in the eye-open time with respect to time, the estimation result is output to the driver, and a drive assist process is performed. However, the gradient determining section (physiological condition change determining unit) 63 may determine the change in the physiological condition of the driver on the basis of the amount of change of the variation in the eye-open time with respect to time. That is, the gradient determining section 63 may determine whether the physiological condition of the driver change on the basis of the gradient of the approximate line indicating the variation in the eye-open time. For example, when the gradient is reduced in the negative direction, the gradient determining section 63 may determine that the arousal level of the driver is rapidly reduced and drowsiness occurs or the driver is in an absentminded condition and perform an appropriate drive assist process at the time when these are determined. On the other hand, when the gradient increases in the positive direction, it may be determined that the driver is in a waking condition and the drive assist process that is being currently performed may be cancelled, or the position of a service area where the vehicle is scheduled to be stopped in order to take a rest may be set so as to be away from the position at the current time.

INDUSTRIAL APPLICABILITY

The invention can be applied to estimate the physiological condition of a target person.

REFERENCE SIGNS LIST 1, 100, 200, 300, 400, 500, 600, 700: VEHICLE CONTROL DEVICE
7: EYE-OPEN TIME ACQUIRING SECTION (EYE-OPEN TIME ACQUIRING UNIT)
8: VARIATION CALCULATING SECTION (VARIATION ACQUIRING UNIT)
9: DROWSINESS PREDICTING SECTION (PHYSIOLOGICAL CONDITION DETERMINING UNIT)

10, 110, 210, 310, 410, 510, 610, 710: PHYSIOLOGICAL CONDITION ESTIMATION DEVICE
15: UNIT TIME WIDTH SETTING SECTION (TIME WIDTH SETTING UNIT)
21: MAXIMUM VALUE DERIVING SECTION (MAXIMUM VALUE DERIVING UNIT)
22: THRESHOLD VALUE SETTING SECTION (THRESHOLD VALUE SETTING UNIT)
31: ATTENTIVENESS-REDUCED CONDITION DETERMINING SECTION (PHYSIOLOGICAL CONDITION DETERMINING UNIT)
32: DROWSINESS OCCURRENCE POSSIBILITY DETERMINING SECTION (DROWSINESS OCCURRENCE POSSIBILITY DETERMINING UNIT)
33: DROWSINESS OCCURRENCE TIME ESTIMATING SECTION (DROWSINESS OCCURRENCE ESTIMATING UNIT)
63: GRADIENT DETERMINING SECTION (PHYSIOLOGICAL CONDITION CHANGE DETERMINING UNIT)
64: SLEEPING OCCURRENCE TIME CALCULATING SECTION (PHYSIOLOGICAL CONDITION ESTIMATING UNIT)
71: SLEEPING PREDICTION OUTPUT EXISTENCE DETERMINING SECTION (ESTIMATION RESULT UPDATE UNIT)
72: AMOUNT OF CHANGE DETERMINING SECTION (ESTIMATION RESULT UPDATE UNIT)
73: GRADIENT COMPARING SECTION (ESTIMATION RESULT UPDATE UNIT)
74: PREDICTION CANCELLATION OUTPUT SECTION (ESTIMATION RESULT UPDATE UNIT)
$Th\_a$, TH ($t0$): AMPLITUDE THRESHOLD VALUE (PREDETERMINED THRESHOLD VALUE)
$tw$, W: UNIT TIME WIDTH (TIME WIDTH)

The invention claimed is:

1. A physiological condition estimation device comprising:
an eye-open time acquiring unit that acquires an eye-open time of a target person;
a variation acquiring unit that acquires a variation in the eye-open time acquired by the eye-open time acquiring unit; and
a physiological condition determining unit that determines a physiological condition of the target person on the basis of the variation in the eye-open time acquired by the variation acquiring unit,
wherein the physiological condition determining unit determines a low arousal level condition before the arousal level is reduced to a value where the target person makes an error, and
the physiological condition determining unit determines the low arousal level condition on the basis of the variation in the eye-open time being less than a predetermined threshold value.

2. The physiological condition estimation device according to claim 1,
wherein the variation acquiring unit performs a statistical process on the eye-open time from a standard deviation or a variance to calculate the variation in the eye-open time.

3. The physiological condition estimation device according to claim 2,
wherein the physiological condition determining unit calculates an average value of the variation in the eye-open time to smooth data and compares the calculated value with the predetermined threshold value to determine the physiological condition.

4. The physiological condition estimation device according to claim 3, further comprising:
a maximum value deriving unit that derives a maximum value of the variation in the eye-open time and updates the maximum value; and
a threshold value setting unit that sets the predetermined threshold value used by the physiological condition determining unit to determine the physiological condition, on the basis of the updated maximum value.

5. The physiological condition estimation device according to claim 2, further comprising:
a time width setting unit that sets a time width which is used by the variation acquiring unit to perform the statistical process, on the basis of data of a plurality of the eye-open times acquired by the eye-open time acquiring unit.

6. The physiological condition estimation device according to claim 1,
wherein, after the physiological condition determining unit determines the condition in which the arousal level is low, the physiological condition estimation device changes an operation mode to a sleeping detection mode in which the drowsiness of the target person is directly detected.

7. The physiological condition estimation device according to claim 1,
wherein the variation acquiring unit counts a number of eye-open times that are longer than the predetermined threshold value and the number of eye-open times that are shorter than the predetermined threshold value among the eye-open times acquired by the eye-open time acquiring unit within a predetermined sampling time, thereby acquiring the variation in the eye-open time.

8. A vehicle control device comprising the physiological condition estimation device according to claim 1.

9. The physiological condition estimation device according to claim 1,
wherein, when a duration time for which the variation in the eye-open time is less than the predetermined threshold value is more than a time threshold value, the physiological condition determining unit determines the low arousal level condition.

10. The physiological condition estimation device comprising:
an eye-open time acquiring unit that acquires an eye-open time of a target person;
a variation acquiring unit that acquires a variation in the eye-open time acquired by the eye-open time acquiring unit; and
a physiological condition determining unit that determines a physiological condition of the target person on the basis of the variation in the eye-open time acquired by the variation acquiring unit,
wherein the physiological condition determining unit determines that the attentiveness is reduced before the target person reaches a drowsy condition, and
the physiological condition determining unit determines the attentiveness reduction on the basis of the variation in the eye-open time being equal to or more than an attentiveness reduction threshold value.

11. The physiological condition estimation device according to claim 10, further comprising:
a drowsiness occurrence possibility determining unit that determines whether there is a possibility of the target person reaching a drowsy condition after the physiological condition determining unit determines that the attentiveness is reduced.

12. The physiological condition estimation device according to claim 11,
wherein the drowsiness occurrence possibility determining unit determines whether there is a possibility of the target person reaching the drowsy condition on the basis of a gradient of an approximate straight line that is set to the variation in the eye-open time.

13. The physiological condition estimation device according to claim 10, further comprising:
a drowsiness occurrence estimating unit that estimates the time until the target person will reach a drowsy condition, on the basis of the amount of change of the variation in the eye-open time with respect to time, after the physiological condition determining unit determines that the attentiveness is reduced.

14. The physiological condition estimation device according to claim 13,
wherein the amount of change of the variation in the eye-open time with respect to time is represented by a gradient of an approximate straight line that is set to the variation in the eye-open time, and
the drowsiness occurrence estimating unit extends the approximate straight line to a future time and estimates the time until the target person will reach the drowsy condition on the basis of the time when the extended approximate straight line is identical to a threshold value.

15. A vehicle control device comprising the physiological condition estimation device according to claim 10.

16. The physiological condition estimation device according to claim 10,
wherein the variation acquiring unit counts a number of eye-open times that are longer than a predetermined threshold value and the number of eye-open times that are shorter than the predetermined threshold value among the eye-open times acquired by the eye-open time acquiring unit within a predetermined sampling time, thereby acquiring the variation in the eye-open time.

17. A physiological condition estimation device comprising:
an eye-open time acquiring unit that acquires an eye-open time of a target person;
a variation acquiring unit that acquires a variation in the eye-open time acquired by the eye-open time acquiring unit; and
a physiological condition estimating unit that estimates a physiological condition of the target person on the basis of an amount of change of the variation in the eye-open time acquired by the variation acquiring unit with respect to time.

18. The physiological condition estimation device according to claim 17,
wherein the physiological condition estimating unit estimates a time required for a change in the physiological condition on the basis of the amount of change of the variation in the eye-open time with respect to time.

19. The physiological condition estimation device according to claim 18, further comprising:
an estimation result update unit that updates the time required for a change in the physiological condition on the basis of an increase or decrease in the amount of change of the variation in the eye-open time with respect to time.

20. The physiological condition estimation device according to claim 18,
wherein the amount of change of the variation in the eye-open time with respect to time is represented by a gradient of an approximate straight line that is set to the variation in the eye-open time, and
the physiological condition determining unit extends the approximate straight line to a future time and estimates the time required for a change in the physiological condition on the basis of the time when the extended approximate straight line is identical to a threshold value.

21. A vehicle control device comprising the physiological condition estimation device according to claim 17.

22. The physiological condition estimation device according to claim 17,
wherein the variation acquiring unit counts a number of eye-open times that are longer than a predetermined threshold value and the number of eye-open times that are shorter than the predetermined threshold value among the eye-open times acquired by the eye-open time acquiring unit within a predetermined sampling time, thereby acquiring the variation in the eye-open time.

23. The physiological condition estimation device according to claim 17,
wherein the amount of change of the variation in the eye-open time with respect to time is represented by a gradient of an approximate straight line that is set to the variation in the eye-open time, and
the physiological condition determining unit determines the physiological condition on the basis of the gradient of the approximate straight line.

24. A physiological condition estimation device comprising:
an eye-open time acquiring unit that acquires an eye-open time of a target person;
a variation acquiring unit that acquires a variation in the eye-open time acquired by the eye-open time acquiring unit; and
a physiological condition change determining unit that determines a change in a physiological condition of the target person on the basis of the amount of change of the variation in the eye-open time acquired by the variation acquiring unit with respect to time.

25. A vehicle control device comprising the physiological condition estimation device according to claim 24.

26. The physiological condition estimation device according to claim 24,
wherein the variation acquiring unit counts a number of eye-open times that are longer than a predetermined threshold value and the number of eye-open times that are shorter than the predetermined threshold value among the eye-open times acquired by the eye-open time acquiring unit within a predetermined sampling time, thereby acquiring the variation in the eye-open time.

27. The physiological condition estimation device according to claim 24,
wherein the amount of change of the variation in the eye-open time with respect to time is represented by a gradient of an approximate straight line that is set to the variation in the eye-open time, and
the physiological condition change determining unit determines a change in the physiological condition of the target person on the basis of the gradient of the approximate straight line.

* * * * *

UNITED STATES PATENT AND TRADEMARK OFFICE
CERTIFICATE OF CORRECTION

| | | |
|---|---|---|
| PATENT NO. | : 8,576,081 B2 | Page 1 of 1 |
| APPLICATION NO. | : 13/201189 | |
| DATED | : November 5, 2013 | |
| INVENTOR(S) | : Y. Hatakeyama et al. | |

It is certified that error appears in the above-identified patent and that said Letters Patent is hereby corrected as shown below:

In the Specifications

Column 26, line 60, change "$A \leq Gt$" to -- $A \geq Gt$ --.

Signed and Sealed this
Thirteenth Day of May, 2014

Michelle K. Lee
*Deputy Director of the United States Patent and Trademark Office*